US009625482B2

(12) United States Patent
Yamada et al.

(10) Patent No.: US 9,625,482 B2
(45) Date of Patent: Apr. 18, 2017

(54) SAMPLE ANALYZER

(71) Applicant: Sysmex Corporation, Kobe-shi, Hyogo (JP)

(72) Inventors: Miyuki Yamada, Kobe (JP); Shuji Kawaguchi, Kobe (JP); Hiroshi Kurono, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 206 days.

(21) Appl. No.: 14/134,735

(22) Filed: Dec. 19, 2013

(65) Prior Publication Data

US 2014/0178251 A1 Jun. 26, 2014

(30) Foreign Application Priority Data

Dec. 21, 2012 (JP) ................................. 2012-279971

(51) Int. Cl.
*G01N 35/10* (2006.01)

(52) U.S. Cl.
CPC ................................ *G01N 35/1011* (2013.01)

(58) Field of Classification Search
None
See application file for complete search history.

(56) References Cited

U.S. PATENT DOCUMENTS

| 2002/0095974 A1* | 7/2002 | Gilson ................... G01N 35/10 73/1.74 |
| 2007/0065945 A1* | 3/2007 | Sigrist ................ G01N 35/1011 436/43 |
| 2009/0226344 A1 | 9/2009 | Nishida et al. |
| 2012/0045366 A1* | 2/2012 | Katsumi ............ G01N 35/1011 422/67 |
| 2012/0222773 A1* | 9/2012 | Yamato .................. G01N 35/10 141/1 |
| 2012/0253693 A1* | 10/2012 | Inomata ........... G01N 35/00663 702/31 |

FOREIGN PATENT DOCUMENTS

| CN | 102384982 A | 3/2012 |
| CN | 102654507 A | 9/2012 |
| CN | 103229059 A | 7/2013 |

(Continued)

*Primary Examiner* — Jill Warden
*Assistant Examiner* — Benjamin Whatley
(74) *Attorney, Agent, or Firm* — Brinks, Gilson & Lione

(57) ABSTRACT

A sample analyzer comprises a container setting part on which a liquid container is to be set, a liquid supplying part configured to supply a liquid to the liquid container, an aspiration tube configured to aspirate a sample or a reagent, a movement mechanism configured to move the aspiration tube, a liquid surface sensor configured to detect contact of the aspiration tube with a liquid surface, and a controller configured to execute an aspiration tube adjustment operation. The aspiration tube adjustment operation comprises supplying the liquid to the liquid container by the liquid supplying part, lowering the aspiration tube by the movement mechanism toward the liquid container set on the container setting part, and obtaining information regarding a position in a height direction of the aspiration tube at a time when the aspiration tube has come into contact with the liquid surface.

13 Claims, 18 Drawing Sheets

(56) References Cited

FOREIGN PATENT DOCUMENTS

| JP | 2001-091522 A | | 4/2001 |
|----|---------------|---|--------|
| JP | 2009-300152 A | | 12/2009 |
| JP | 2010-236967 A | | 10/2010 |
| JP | 2010236967 A | * | 10/2010 |
| JP | 2012-042294 A | | 3/2012 |
| JP | 2012-208099 A | | 10/2012 |

* cited by examiner

F I G. 1 4
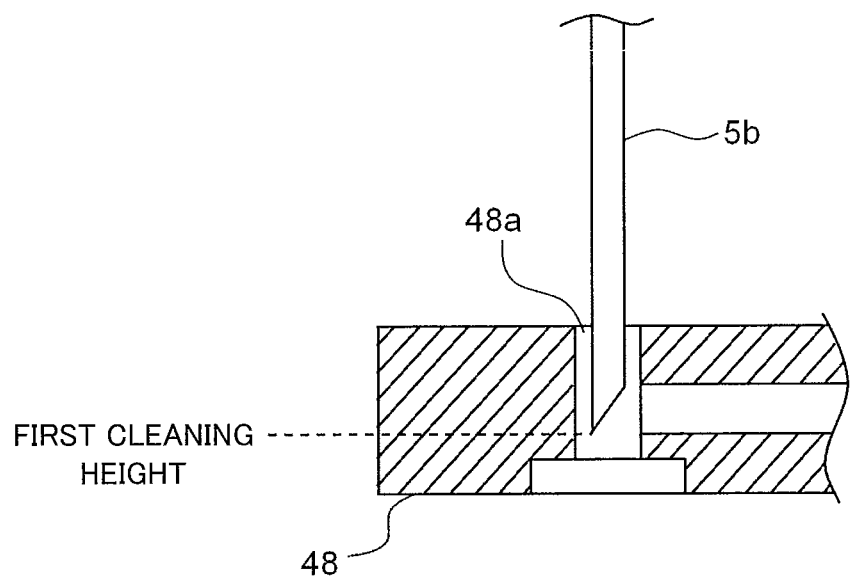

FIG. 16
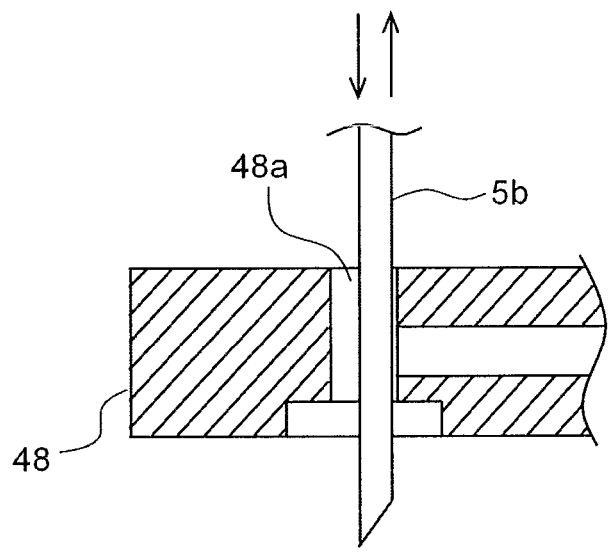
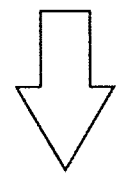
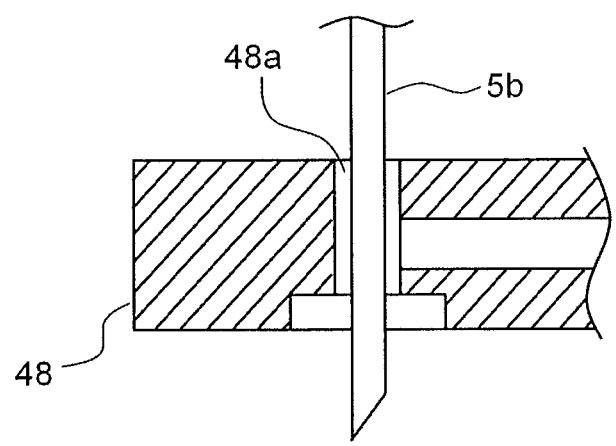

SAMPLE ANALYZER

RELATED APPLICATIONS

This application claims priority under 35 U.S.C. §119 to Japanese Patent Application No. 2012-279971 filed on Dec. 21, 2012, the entire content of which is hereby incorporated by reference.

FIELD OF THE INVENTION

The present invention relates to a sample analyzer which aspirates a liquid such as a sample, a reagent, or the like, using an aspiration tube.

BACKGROUND OF THE INVENTION

To date, there have been known sample analyzers which mix a sample with a reagent and analyze components or characteristics of the sample. In such a sample analyzer, an aspiration tube is used which aspirates a liquid from a container containing a liquid such as a sample or a reagent. Here, in the course of the sample analyzer performing sample analysis, there are cases where the aspiration tube is worn, deformed due to a collision, or the like, or a mounting position of the aspiration tube is displaced. In a case where the aspiration tube has been worn, deformed due to a collision, or the like and the aspiration tube has been replaced with a new one, or in a case where the mounting position of the aspiration tube has been displaced, position adjustment needs to be performed such that the aspiration tube can properly perform aspiration.

Japanese Laid-Open Patent Application No. 2001-91522 describes a technology for performing position adjustment of a replaced probe in which, when a probe is replaced, the replaced probe is lowered toward a projection for automatic adjustment so as to collide with the projection, whereby the height of the replaced probe is detected.

However, the apparatus described in Japanese Laid-Open Patent Application No. 2001-91522 is configured such that the probe is caused to collide with the projection for positioning. Thus, there is a risk of the probe being deformed or damaged due to the collision with the projection.

SUMMARY OF THE INVENTION

The scope of the present invention is defined solely by the appended claims, and is not affected to any degree by the statements within this summary.

A first aspect of the present invention is a sample analyzer comprising a container setting part on which a liquid container is to be set, a liquid supplying part configured to supply a liquid to the liquid container, an aspiration tube configured to aspirate a sample or a reagent, a movement mechanism configured to move the aspiration tube, a liquid surface sensor configured to detect contact of the aspiration tube with a liquid surface, and a controller configured to execute an aspiration tube adjustment operation. The aspiration tube adjustment operation comprises supplying the liquid to the liquid container by the liquid supplying part, lowering the aspiration tube by the movement mechanism toward the liquid container set on the container setting part, and obtaining information regarding a position in a height direction of the aspiration tube at a time when the aspiration tube has come into contact with the liquid surface.

A second aspect of the present invention is a sample analyzer comprising a liquid containing part configured to contain a liquid, a liquid supplying part configured to supply the liquid to the liquid containing part, an aspiration tube configured to aspirate a sample or a reagent, a movement mechanism configured to move the aspiration tube, a liquid surface sensor configured to detect contact of the aspiration tube with a liquid surface, and a controller configured to execute an aspiration tube adjustment operation. The aspiration tube adjustment operation comprises supplying the liquid to the liquid containing part by the liquid supplying part, lowering the aspiration tube by the movement mechanism toward the liquid containing part set on the container setting part, and obtaining information regarding a position in a height direction of the aspiration tube at a time when the aspiration tube has come into contact with the liquid surface.

A third aspect of the present invention is a sample analyzer which analyzes a measurement specimen prepared from a sample and a reagent, the sample analyzer comprising an aspiration tube configured to aspirate the sample or the reagent, a movement mechanism configured to move the aspiration tube, and a controller configured to execute operations. The operations comprises moving, upon receiving an input for executing an aspiration tube adjustment operation, the aspiration tube to an aspiration tube replacement position for replacing the aspiration tube, and controlling, after power of the sample analyzer has been turned off and the aspiration tube has been replaced, the movement mechanism so as to execute the aspiration tube adjustment operation when the power of the sample analyzer is turned on.

BRIEF DESCRIPTION OF THE DRAWINGS

FIG. 14 is an enlarged side cross-sectional view of a piercer cleaning part for describing a cleaning height;

FIG. 16 is an enlarged side cross-sectional view of the piercer cleaning part for describing positioning of a piercer at a sample aspiration position;

DETAILED DESCRIPTION OF THE PREFERRED EMBODIMENTS

The preferred embodiments of the present invention will be described hereinafter with reference to the drawings.

<Structure of Sample Analyzer>

Figure 1:
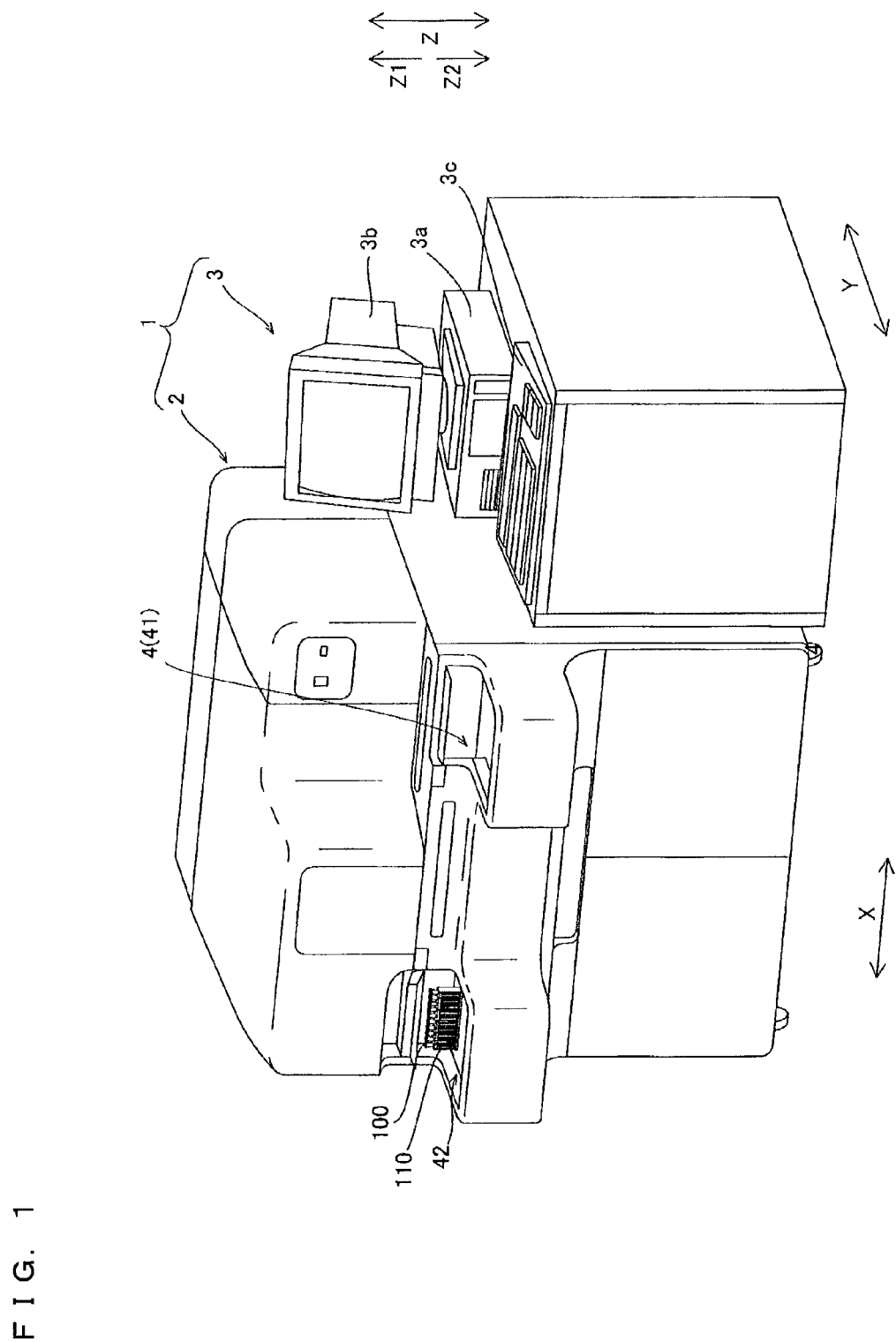
FIG. 1 is a perspective view showing an external structure of a sample analyzer according to an embodiment.
Figure 2:
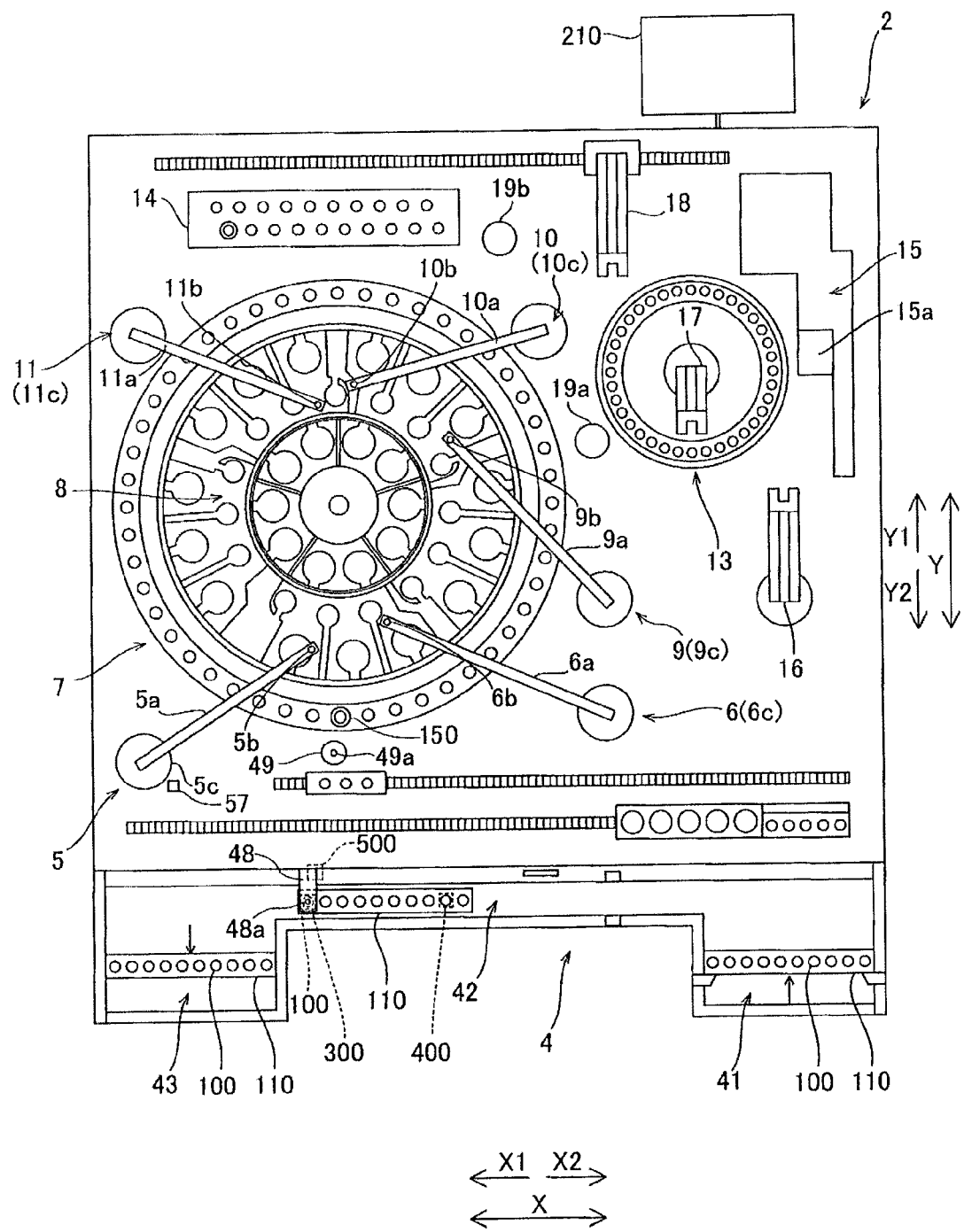
FIG. 2 is a plan view showing a structure of the sample analyzer according to an embodiment.

FIG. 1 is a perspective view showing an external structure of a sample analyzer according to the present embodiment, and FIG. 2 is a plan view showing a structure of the sample analyzer. A sample analyzer 1 is a blood coagulation analyzer which performs optical measurement and analysis of a sample by using a coagulation method, a synthetic substrate method, immunonephelometry, and an agglutination method, by illuminating with light a measurement specimen prepared by adding a reagent to plasma being a sample.

As shown in FIG. 1, the sample analyzer 1 includes a measurement mechanism unit 2 which optically measures components contained in a sample, and a control device 3 being a personal computer electrically connected to the measurement mechanism unit 2. The control device 3 is implemented by the computer composed mainly of a controller 3a, a display unit 3b, and an input unit 3c including a key board and a mouse. The control device 3 has a function of transmitting, to the measurement mechanism unit 2, a start instruction, an end instruction, and the like regarding sample analysis operation based on operation inputs, and a function of receiving various types of reports such as a drive stop report and an error report, analysis results, and the like, from the measurement mechanism unit 2. Further, the control device 3 has a function of displaying, on the display unit 3b, the received error report and analysis results obtained based on detection values by the measurement mechanism unit 2, and the like.

As shown in FIG. 2, the measurement mechanism unit 2 includes a sample transport part (sampler) 4, a first sample dispensing arm 5, a second sample dispensing arm 6, a cuvette (reaction container) setting part 7 and a reagent setting part 8, reagent dispensing arms 9, 10, and 11, a reaction part 13, a detection part 14, a cuvette supplying part 15, and catcher units 16, 17, and 18. Further, the measurement mechanism unit 2 is connected to an RO water tank 210 which holds RO water therein.

The sample transport part 4 includes a rack stocker 41, a rack transporter 42, and a rack collection part 43. The rack stocker 41 has a function of stocking a rack 110 (see FIG. 1) on which a plurality of sample containers 100 each containing a sample are placed, and a function of sending out the rack 110 to the rack transporter 42. The rack transporter 42 is provided so as to extend in the X direction to connect the rack stocker 41 and the rack collection part 43. By driving a transport mechanism not shown, the rack transporter 42 can transport a sample container 100 which is placed on the rack 110 and which is to be analyzed, to a sample aspiration position 300 for the first sample dispensing arm 5 or a sample aspiration position 400 for the second sample dispensing arm 6. Further, the rack collection part 43 has a function of collecting, from the rack transporter 42, a rack 110 holding sample containers 100 for which dispensing has been ended.

Figure 4:
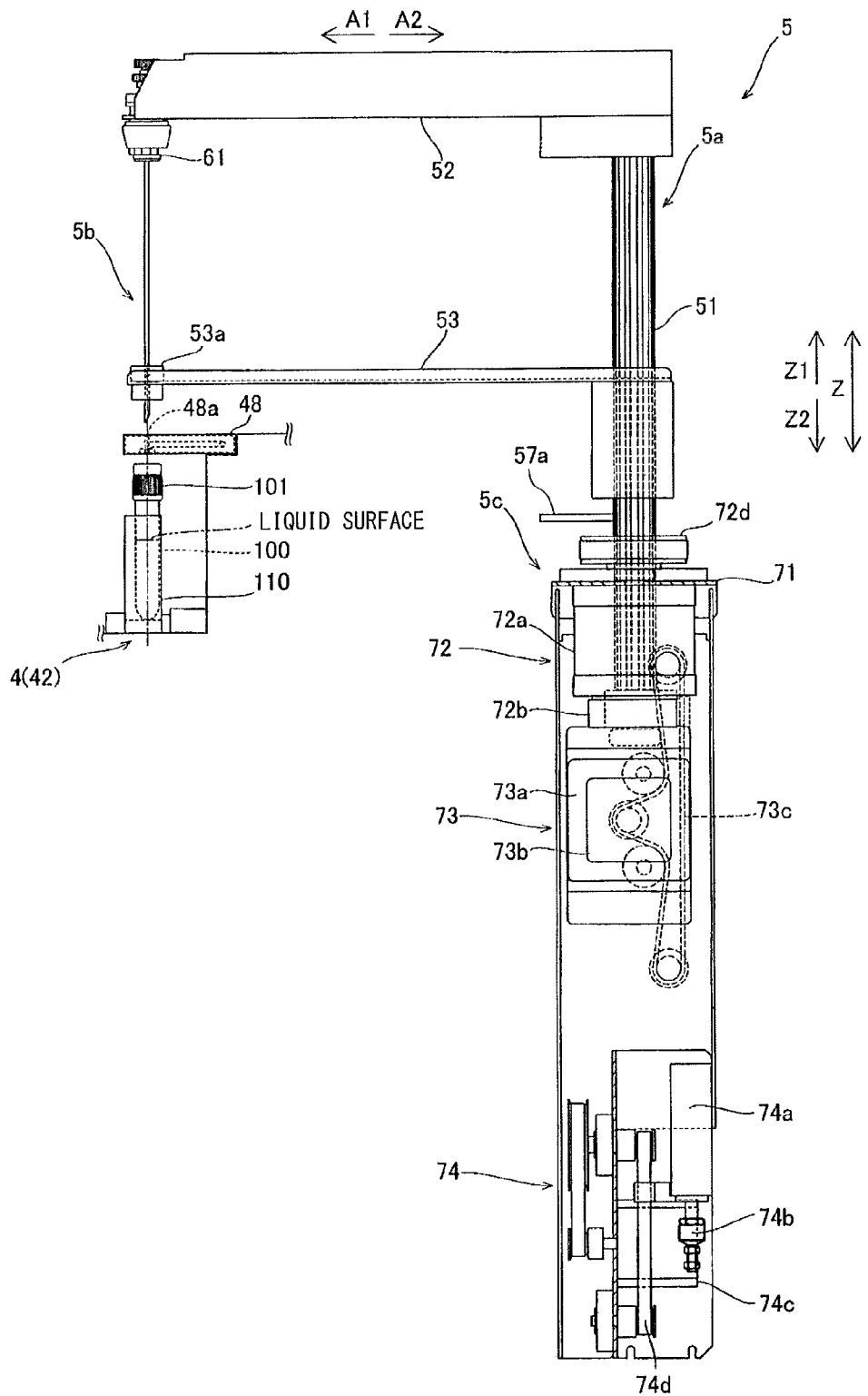
FIG. 4 is a side view showing a structure of a first sample dispensing arm.
Figure 5:
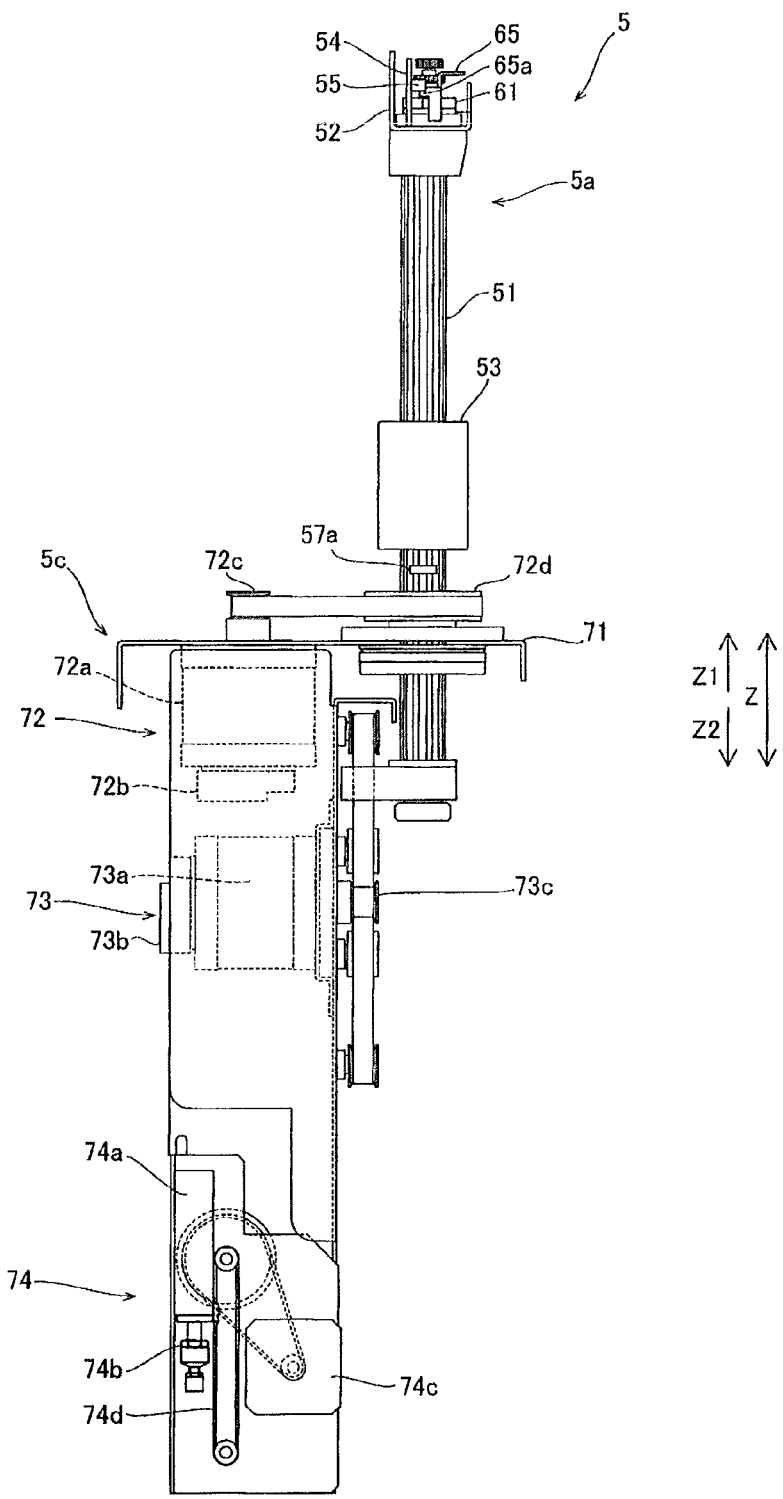
FIG. 5 is a rear view showing a structure of the first sample dispensing arm.
Figure 6:
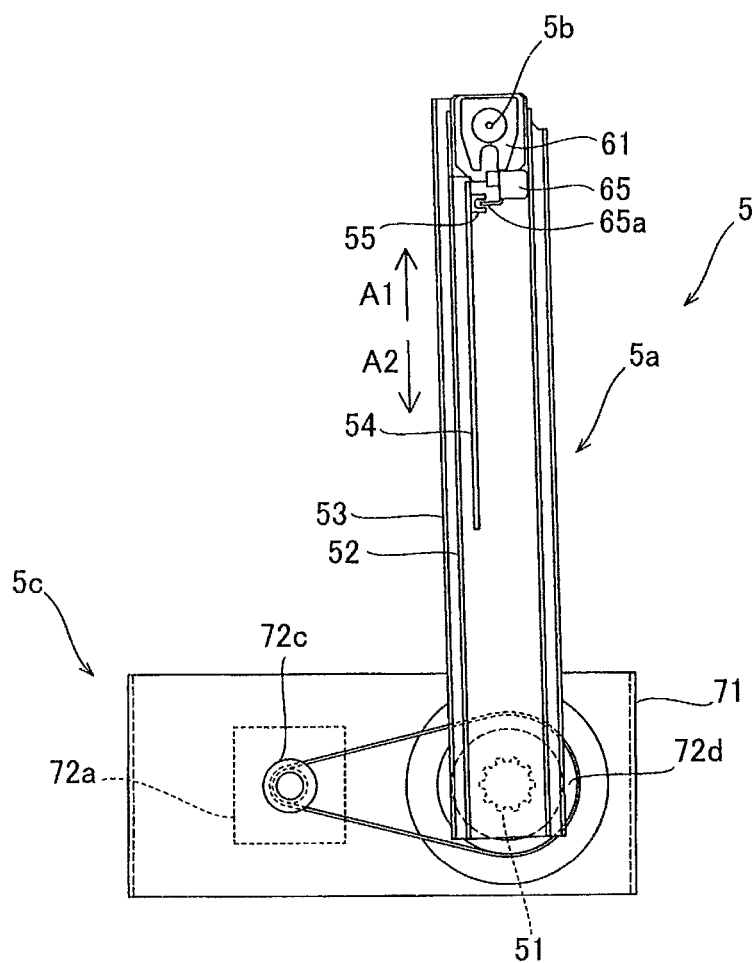
FIG. 6 is a plan view showing a structure of the first sample dispensing arm.

The rack transporter 42 is provided with a piercer cleaning part 48. As shown in FIG. 4, the piercer cleaning part 48 is provided at a position above the sample aspiration position 300 of the rack transporter 42. As shown in FIG. 4 to FIG. 6, the piercer cleaning part 48 includes an aspiration tube path 48a passing therethrough in the up-down (Z direction), and is configured such that a later-described piercer 5b of the first sample dispensing arm 5 passes through the aspiration tube path 48a when the piercer 5b aspirates a sample from a sample container 100. The piercer cleaning part 48 is connected to the RO water tank 210, and has a function of cleaning the piercer 5b by discharging and aspirating a cleaning liquid therein when the piercer 5b passes through the aspiration tube path 48a. Further, the piercer cleaning part 48 is provided so as to be movable in the up-down direction. The piercer cleaning part 48 is raised or lowered by the controller 3a driving a motor not shown. By being movable in the up-down direction in this manner, the piercer cleaning part 48 also has a function of downwardly pressing a cap 101 of a sample container 100.

To the front of the cuvette setting part 7 of the measurement mechanism unit 2, a piercer cleaning part 49 for cleaning the piercer 5b is provided. This piercer cleaning part 49 is provided with an aspiration tube path 49a passing therethrough in the up-down direction (Z direction), and allows the piercer 5b of the first sample dispensing arm 5 to be inserted in the aspiration tube path 49a when the first sample dispensing arm 5 is lowered. The piercer cleaning part 49 is connected to the RO water tank 210, and has a function of cleaning the piercer 5b by discharging and aspirating RO water used as a cleaning liquid, with the piercer 5b being inserted in the aspiration tube path 49a.

In the present embodiment, the first sample dispensing arm 5 includes an arm part 5a, the piercer 5b being an aspiration tube, and a body part 5c, and has a function of aspirating a sample in a sample container 100 transported to the sample aspiration position 300 by the sample transport part 4, and a function of discharging the sample by a predetermined amount into a cuvette 150 set in the cuvette setting part 7. The detailed structure of the first sample dispensing arm 5 will be described later.

The second sample dispensing arm 6 includes an arm part 6a, a pipette 6b being an aspiration tube, and a body part 6c, and has a function of aspirating a sample in a sample container 100 transported to the sample aspiration position 400 by the sample transport part 4, and a function of discharging the sample by a predetermined amount into a cuvette 150 set in the cuvette setting part 7. The pipette 6b is different from the piercer 5b and is a tube whose lower end edge is not sharp but horizontal. The pipette 6b is connected to the RO water tank 210 described above, and RO water used as a cleaning liquid can be supplied to the pipette 6b.

The reagent setting part 8 is provided for setting therein reagent containers containing various types of reagents, diluents, and the like to be used in measurement.

The reagent dispensing arms 9, 10, and 11 have a function of aspirating reagents in reagent containers not shown set in the reagent setting part 8 and a function of dispensing predetermined reagents into cuvettes 150 set in the cuvette setting part 7, respectively. The reagent dispensing arms 9, 10, and 11 include arm parts 9a, 10a, and 11a, pipettes 9b, 10b, and 11b being aspiration tubes, and body parts 9c, 10c, and 11c, respectively. The reagent dispensing arms 9, 10, and 11 are configured to pivot the arm parts 9a, 10a, and 11a, by means of the body parts 9c, 10c, and 11c, position the pipettes 9b, 10b, and 11b above reagent containers or above cuvettes 150, and raise/lower the arm parts 9a, 10a, and 11a by means of the body parts 9c, 10c, and 11c, thereby performing aspiration operation and discharge operation of reagents by means of the pipettes 9b, 10b, and 11b, respectively.

The reaction part 13 is formed in an annular shape so as to surround the catcher unit 17, and is configured to be able to hold a plurality of cuvettes 150. The reaction part 13 has a function of heating cuvettes 150 that have been set. That is, in the reaction part 13, a specimen being a mixture of a sample and reagents contained in each cuvette 150 is heated, whereby reaction between the sample and the various types of reagents in the cuvette 150 is promoted.

The detection part 14 has a function of performing optical measurement on a measurement specimen after the reaction between the sample and the various types of reagents has ended in the reaction part 13, thereby detecting optical information reflecting components contained in the measurement specimen.

The cuvette supplying part 15 is configured to be able to house a plurality of cuvettes 150, and to be able to sequentially supply cuvettes 150 to a cuvette stocker 15a. Here, the plurality of cuvettes 150 housed in the cuvette supplying part 15 each have an identical shape. Each cuvette 150 has a bottom and has a substantially cylindrical shape. The cuvette 150 is provided, at its upper end, with a flange to be gripped by the catcher unit 16, 17, or 18 described later when the cuvette 150 is transported by the catcher unit 16, 17, or 18.

The catcher units 16, 17, and 18 each have a function of gripping and transporting a cuvette 150. The catcher unit 17 has a function of taking a cuvette 150 out of the cuvette stocker 15a to set the cuvette 150 in the cuvette setting part 7, and a function of transporting the cuvette from the cuvette setting part 7 to the reaction part 13. The catcher unit 18 has a function of transporting a cuvette 150 from the reaction part 13 to the detection part 14. The catcher unit 17 and the catcher unit 18 have functions of discarding cuvettes 150 that have been used, into a discarding hole 19a and a discarding hole 19b, respectively.

Figure 3:
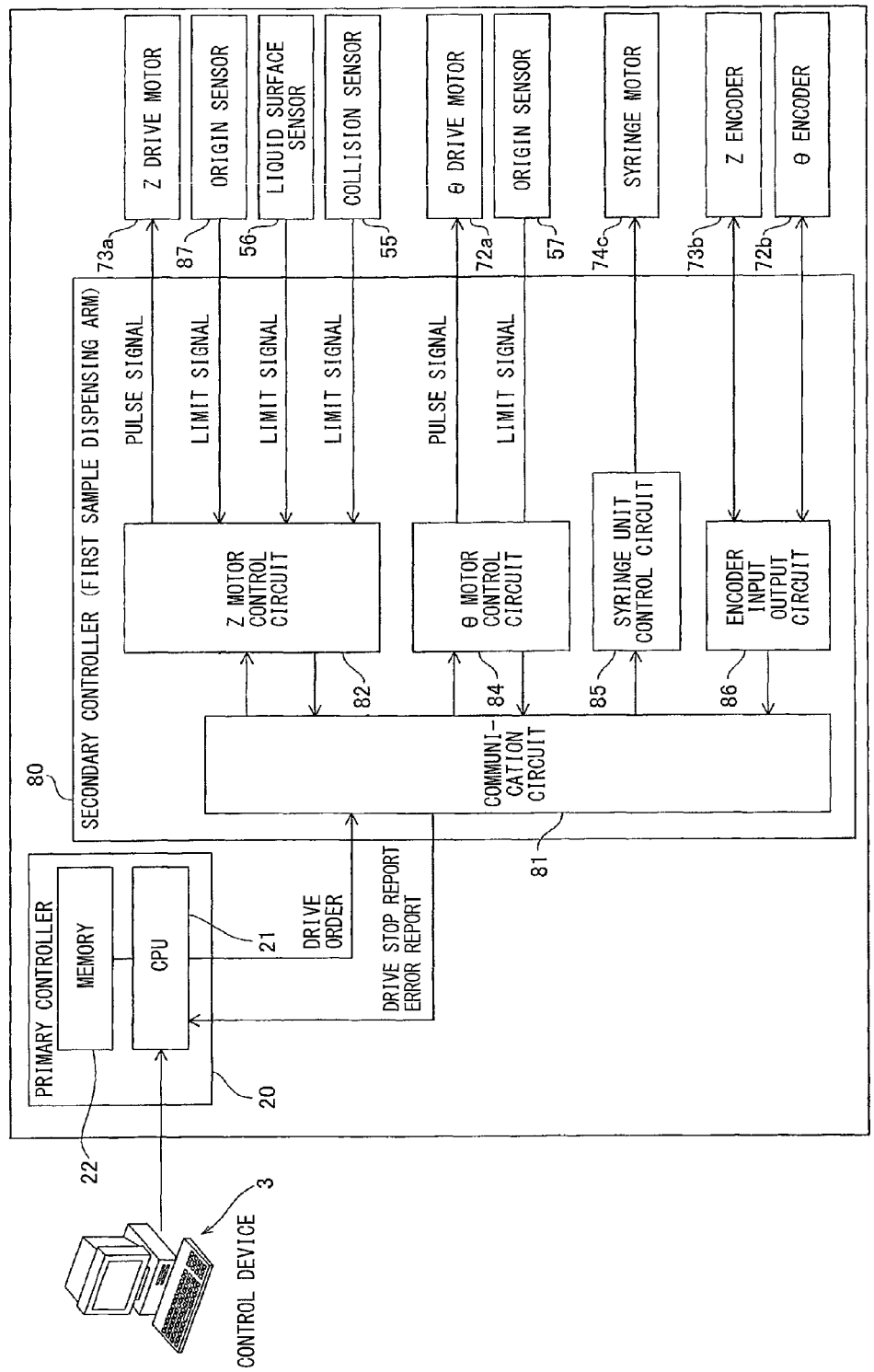
FIG. 3 is a block diagram showing a configuration of a controller of a measurement mechanism unit.

FIG. 3 is a block diagram showing a configuration of a controller of the measurement mechanism unit. As shown in FIG. 3, the measurement mechanism unit 2 includes a primary controller 20, and a secondary controller for controlling operation of mechanisms such as various types of dispensing arms (e.g. the first sample dispensing arm 5), the reaction part 13, the reagent setting part 8, the catcher units 16 to 18, and the like. Here, only a secondary controller 80 of the first sample dispensing arm 5 is illustrated in FIG. 3. The mechanisms such as the various types of dispensing arms, the reaction part 13, the cuvette setting part 7, the reagent setting part 8, the catcher units 16 to 18, and the like are controlled by their respective secondary controllers, based on drive instructions from the primary controller 20. The sample transport part 4 is also configured to be controlled by the primary controller 20.

As shown in FIG. 3, the primary controller 20 includes a CPU 21 and a memory 22. As shown in FIG. 1, the primary controller 20 is connected to the control device 3 and has a function of transmitting, to the control device 3, optical information of a sample as measurement data, and a function of receiving a signal from the controller 3a of the control device 3. Further, the primary controller 20 has a function of transmitting drive orders by means of the CPU 21 to components of the sample transport part 4 and the measurement mechanism unit 2, and a function of receiving drive stop reports and error reports from the components. It is configured such that the received drive stop reports and error reports from the components are transmitted from the primary controller 20 to the control device 3.

Next, a structure of the first sample dispensing arm 5 according to the present embodiment will be described in detail. Moreover, the secondary controller 80 of the first sample dispensing arm 5 will also be described. In the present embodiment, only the secondary controller 80 of the first sample dispensing arm 5 will be described, and description of the other secondary controllers will be omitted.

FIG. 4 is a side view showing a structure of the first sample dispensing arm, FIG. 5 is a rear view thereof, and FIG. 6 is a plan view thereof. The first sample dispensing arm 5 is configured to: arrange the piercer 5b above the sample aspiration position 300 by the body part 5c pivot-driving the arm part 5a as shown in FIG. 2; and then, to lower the arm part 5a by means of the body part 5c as shown in FIG. 4; thereby to insert the piercer 5b into a sample container 100 arranged at the sample aspiration position 300, to aspirate the sample. Further, the first sample dispensing arm 5 is configured to: pull the piercer 5b out of the sample container 100 by raising the arm part 5a; to pivot the arm part 5a to position the piercer 5b at a dispensing position above a cuvette 150 set in the cuvette setting part 7; and then to discharge the sample by a predetermined amount.

As shown in FIG. 4 to FIG. 6, the arm part 5a includes a shaft part 51, a support member 52, and a guide part 53. The arm part 5a is configured such that: the entirety including the shaft part 51, the support member 52, and the guide part 53 is pivoted and raised/lowered by means of a θ drive motor 72a and a Z drive motor 73a of the body part 5c. The support member 52 is fixed to the upper end of the shaft part 51, and the shaft part 51 is supported by the body part 5c so as to be rotatable about the shaft and to be able to be raised/lowered.

As shown in FIG. 5, the support member 52 is a frame made of a metal plate extending in the horizontal direction and having a substantially U-shaped cross section, and is mounted, at its base portion on an arrow A2 direction side, to the upper end of the shaft part 51. The piercer 5b is mounted to a leading end of the support member 52 on an arrow A1 direction side, so as to extend downwardly therefrom and to be movable upwardly relative to the support member 52. Further, as shown in FIG. 6, in the support member 52, a control board 54 including the secondary controller 80 of the first sample dispensing arm 5 is set. The control board 54 is provided with a collision sensor 55 of an optical type having a light emitter and a light receiver. As described later, the collision sensor 55 is configured to detect rising of the piercer 5b relative to the support member 52, by detecting a detection piece 65a of a member-to-be-detected 65 which moves along with the piercer 5b. Further, as shown in FIG. 3, the control board 54 is provided with a liquid surface sensor 56 of a capacitance type using the piercer 5b as an electrode, and is configured to be able to detect that the tip of the piercer 5b has come into contact with the liquid surface.

As shown in FIG. 4, the guide part 53 is arranged below the support member 52 and provided in parallel with the support member 52. The base portion of the guide part 53 is fixedly mounted to the shaft part 51. A pipette guide 53a having a through hole extending in the up-down direction being the Z direction shown in FIG. 4 is provided to the leading end of the guide part 53, and is mounted with the piercer 5b inserted therethrough. Thus, it is configured such that the piercer 5b is guided downwardly being an arrow Z2 direction.

The piercer 5b is a metal tube member, and is mounted to the support member 52 so as to extend downwardly. Further, the lower end of the piercer 5b is formed sharp so as to be able to pass through the cap 101 of a sample container 100. Further, the piercer 5b is held so as to hang down, by a holding member 61 provided at the leading end of the support member 52. As shown in FIG. 4, the piercer 5b is connected to a syringe unit 74 via a tube. Accordingly, a sample can be aspirated and discharged from the tip of the piercer 5b.

The member-to-be-detected 65 is mounted to the support member 52. As shown in FIG. 6, the member-to-be-detected 65 is arranged so as to face the control board 54 provided with the collision sensor 55. The member-to-be-detected 65 is integrally provided with the detection piece 65a formed so as to extend toward the collision sensor 55 side facing the member-to-be-detected 65. When the piercer 5b collides with an obstacle, the detection piece 65a is moved upwardly to block light in the collision sensor 55, whereby collision of the piercer 5b is detected.

As shown in FIG. 4 and FIG. 5, a member-to-be-detected 57a having a plate-like shape is provided on a side face of the shaft part 51 so as to protrude therefrom. As shown in FIG. 2, the measurement mechanism unit 2 has an origin sensor 57 at a position near the body part 5c of the first sample dispensing arm 5. As shown in FIG. 2, the origin sensor 57 is an optical-type sensor having a light emitter and a light receiver. When the arm part 5a is pivoted and reaches a predetermined origin position 500, the member-to-be-detected 57a blocks light in the origin sensor 57. Accordingly, that the piercer 5b has reached the origin position 500 is detected. The member-to-be-detected 57a has a wide plate-like shape. Accordingly, light in the origin sensor 57 is blocked by the member-to-be-detected 57a in a certain pivot range of the arm part 5a, and this pivot range includes the origin position 500 and the sample aspiration position 300. Therefore, also when the piercer 5b is at the sample aspiration position 300, light in the origin sensor 57 is blocked. That is, by light in the origin sensor 57 not being blocked, it is detected that the piercer 5b is neither at the sample aspiration position 300 nor the origin position 500.

As shown in FIG. 4 and FIG. 5, the body part 5c includes a chassis part 71 which supports the shaft part 51 so as to be able to be rotated and raised/lowered, a rotation mechanism part 72 for rotating the shaft part 51, a raising/lowering mechanism part 73 for raising/lowering the shaft part 51, and the syringe unit 74 for aspirating and discharging a sample from the piercer 5b. The chassis part 71 supports the shaft part 51 to as to be rotatable and movable in the up-down direction.

The rotation mechanism part 72 includes the θ drive motor 72a implemented by a stepping motor, and a θ encoder 72b which detects a rotation position of the θ drive motor 72a. As shown in FIG. 5 and FIG. 6, pulley 72d and 72c are mounted to the shaft part 51 and the output shaft of the θ drive motor 72a, respectively, and it is configured such that the θ drive motor 72a causes the arm part 5a to pivot about the shaft part 51.

As shown in FIG. 4, the raising/lowering mechanism part 73 includes the Z drive motor 73a implemented by a stepping motor, and a Z encoder 73b which detects a rotation position of the Z drive motor 73a. Further, a power transmission mechanism 73c composed of a plurality of pulleys and drive belts is mounted to the output shaft of the Z drive motor 73a, and it is configured such that the Z drive motor 73a causes the arm part 5a to be raised/lowered in the up-down direction.

The syringe unit 74 includes a syringe 74a, a plunger 74b, and a syringe motor 74c for causing the plunger 74b to advance/retract. A tube not shown is connected to the syringe 74a and extends through the shaft part 51 to communicate with the piercer 5b. Further, in the syringe unit 74, the syringe motor 74c and the plunger 74b are connected to a power transmission mechanism 74d composed of a plurality of pulleys and drive belts. Accordingly, drive of the syringe motor 74c can cause the plunger 74b to advance/retract relative to the syringe 74a, thereby allowing aspiration and discharge of a sample via the piercer 5b. Further, the syringe unit 74 is connected to the RO water tank 210 and can supply, to the piercer 5b, RO water to be used as a cleaning liquid.

As shown in FIG. 3, the secondary controller 80 of the first sample dispensing arm 5 includes a communication circuit 81, a Z motor control circuit 82, a θ motor control circuit 84, a syringe unit control circuit 85, and an encoder input output circuit 86.

The communication circuit 81 has: a function of communicating with the primary controller 20; a function of receiving, from the CPU 21 of the primary controller 20, a Z direction drive order and a pivot (θ) direction drive order regarding the first sample dispensing arm 5 and a drive order regarding the syringe unit 74, associated with analysis operation; and a function of transmitting, to the primary controller 20, a drive stop report and an error report regarding the first sample dispensing arm 5. The communication circuit 81 outputs the received drive orders to the Z motor control circuit 82, the θ motor control circuit 84, and the syringe unit control circuit 85, respectively.

The Z motor control circuit 82 has a function of controlling raising/lowering operation in the up-down direction of the arm part 5a performed by the Z drive motor 73a, by outputting a pulse signal corresponding to the Z direction drive order, to the Z drive motor 73a. Further, the Z motor control circuit 82 is configured to receive limit signals as detection signals from an origin sensor 87 for detecting an origin position being an upper limit position in the Z direction of the arm part 5a, the collision sensor 55, and the liquid surface sensor 56, respectively. Upon receiving any of these limit signals during drive of the Z drive motor 73a, the Z motor control circuit 82 stops output of the pulse signal to the Z drive motor 73a. As a result, drive of the Z drive motor 73a is stopped.

It should be noted that the secondary controller 80 is formed by an FPGA (Field Programmable Gate Array). The Z motor control circuit 82 is a hardware circuit constructed by an FPGA, and stops output of a pulse signal immediately upon latch of a limit signal. Thus, stopping of drive of the Z drive motor 73a is performed without waiting for determination to be made by the primary controller 20, and only a drive stop report which reports that drive of the Z drive motor 73a has been stopped is sent to the primary controller 20.

The θ motor control circuit 84 has a function of controlling pivot operation of the arm part 5a performed by the θ drive motor 72a, by outputting a pulse signal corresponding to a pivot (θ) direction drive order, to the θ drive motor 72a. Further, the θ motor control circuit 84 is configured to receive a limit signal from the origin sensor 57 for detecting the origin position 500 in the θ direction of the arm part 5a. Upon receiving this limit signal during drive of the θ drive motor 72a, the θ motor control circuit 84 stops output of the pulse signal to the θ drive motor 72a. As a result, drive of the θ drive motor 72a is stopped.

The syringe unit control circuit 85 has a function of controlling drive operation of the syringe motor 74c in accordance with a drive order of aspiration operation or discharge operation regarding the syringe unit 74.

The encoder input output circuit 86 has a function of receiving an output signal regarding rotation position information of the Z drive motor 73a from the Z encoder 73b and an output signal regarding rotation position information of the θ drive motor 72a from the θ encoder 72b, and a function of outputting the received output signals to the primary controller 20 via the communication circuit 81. Accordingly, it is possible to confirm that the arm part 5a has moved in the up-down direction and the pivot direction in accordance with the drive instructions from the primary controller 20, and to accurately position the piercer 5b above the sample aspiration position 300.

<Operation of Sample Analyzer>

Figure 7:
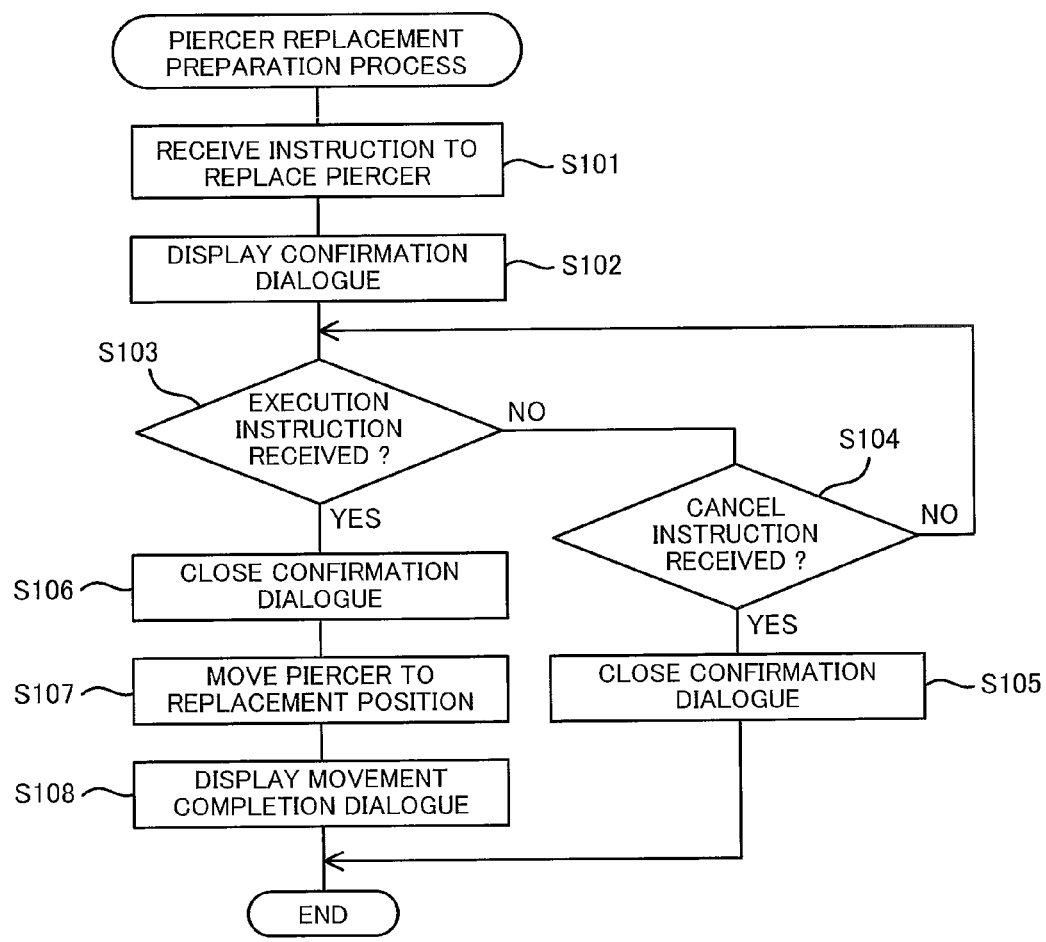
FIG. 7 is a flow chart showing a procedure of a piercer replacement preparation process for the sample analyzer according to an embodiment.

Next, operation of the sample analyzer 1 according to the present embodiment will be described. The primary controller 20 of the sample analyzer 1 according to the present embodiment executes a piercer replacement preparation process and a post-piercer-replacement adjustment process as described below, when the piercer 5b is replaced. FIG. 7 is a flow chart showing the procedure of the piercer replacement preparation process for the sample analyzer 1 according to the present embodiment. The piercer replacement preparation process is a process for shifting the state of the measurement mechanism unit 2 into a state where a user can perform a piercer replacing operation.

When replacing the piercer 5b, the user operates the input unit 3c of the control device 3 to give an instruction to replace the piercer, to the sample analyzer 1. When the CPU of the controller 3a has received the instruction to replace the piercer (S101), the CPU of the controller 3a causes the display unit 3b to display a confirmation dialogue (S102).

Figure 8:
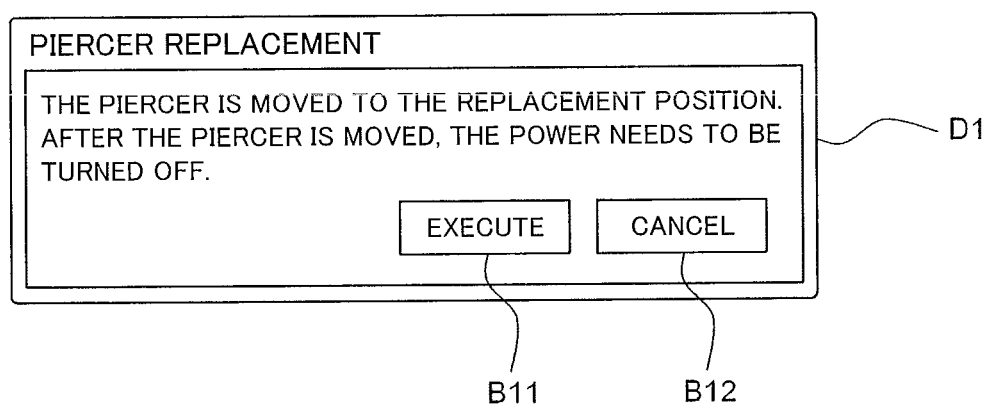
FIG. 8 shows a confirmation dialogue.

FIG. 8 shows the confirmation dialogue. A confirmation dialogue D1 includes message information for notifying the user that the piercer is to be moved to a replacement position, and after the piercer has been moved to the replacement position, power of the sample analyzer 1 needs to be turned off. Moreover, the confirmation dialogue D1 is provided with an execution button B11 and a cancel button B12 selectable by means of the input unit 3c.

The CPU of the controller 3a determines whether an execution instruction has been given from the user (S103). When no execution instruction has been received from the user (NO in S103), the CPU of the controller 3a determines whether a cancel instruction of the piercer replacement preparation process has been received (S104). When no cancel instruction has been received, the CPU of the controller 3a returns the processing to step S103. When the cancel button B12 has been selected by the user and a cancel instruction has been given to the controller 3a, the CPU closes the confirmation dialogue D1 (S105) and ends the processing.

When the execution button B11 has been selected by the user and an execution instruction has been given to the controller 3a (S103), the CPU of the controller 3a closes the confirmation dialogue D1 (S106), and provides instruction data for moving the piercer to the replacement position, to the primary controller 20 of the measurement mechanism unit 2. Accordingly, the CPU 21 of the primary controller 20 controls the first sample dispensing arm 5 to move the piercer 5b to the replacement position (S107).

The replacement position of the piercer 5b is a position where the tip of the piercer 5b is inserted in the aspiration tube path 48a of the piercer cleaning part 48. Upon the piercer 5b having been moved to the replacement position, the primary controller 20 provides data for making notification of this, to the controller 3a, and the CPU of the controller 3a causes the display unit 3b to display a movement completion dialogue (S108), and ends the processing.

Figure 9:
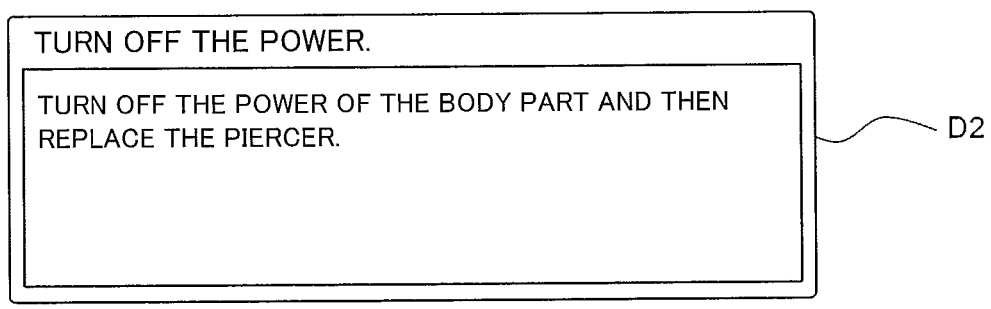
FIG. 9 shows a movement completion dialogue.

FIG. 9 shows the movement completion dialogue. A movement completion dialogue D2 includes a message that instructs the user to turn off the power of the sample analyzer 1 and then replace the piercer 5b. The user confirms the movement completion dialogue D2, and then turns off the power of the sample analyzer 1.

After the power of the sample analyzer 1 has been turned off, the user removes the piercer 5b that has been used from the first sample dispensing arm 5, and mounts a new piercer 5b by using a predetermined replacing jig or the like. At this time, the user inserts the tip of the new piercer 5b into the aspiration tube path 48a of the piercer cleaning part 48. In order to normally perform sample analysis, after replacement of the piercer 5b, it is necessary that the piercer 5b can be accurately moved to the sample aspiration position 300, a sample dispensing position being a predetermined position on the cuvette setting part 7, a cleaning position of the piercer cleaning part 49, or the like, as before the replacement. For this, it is necessary to set the distance, specifically, the number of pulses of the θ drive motor, from the origin position 500 to each of the above positions, as a new adjustment value after the replacement. As described above, by the user mounting the new piercer 5b to the first sample dispensing arm 5 so as to be positioned at the replacement position, the above-described adjustment values can be set through a simple process after the replacement.

Figure 10:
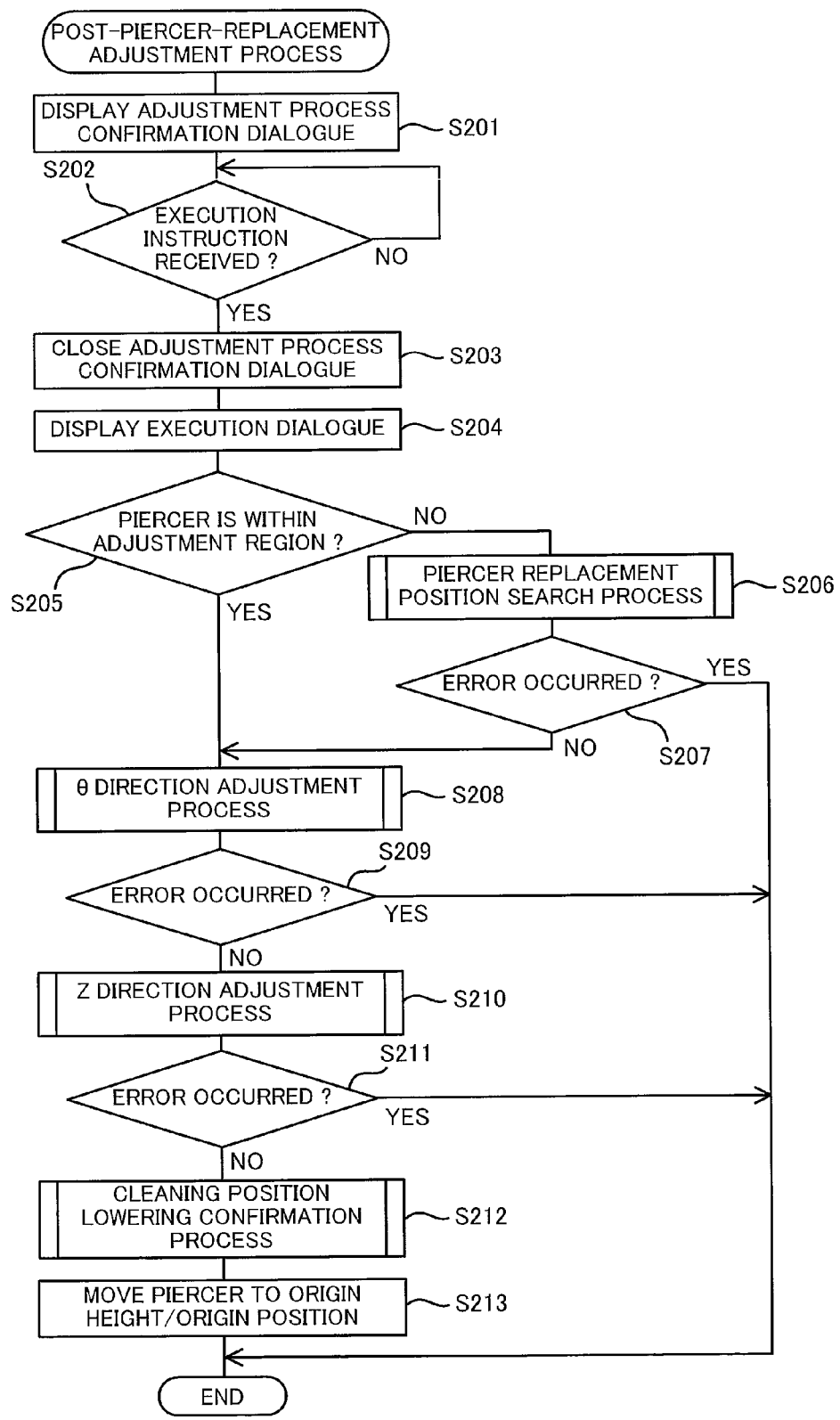
FIG. 10 is a flow chart showing a procedure of a post-piercer-replacement adjustment process for a sample analyzer according to an embodiment.
Figure 11:
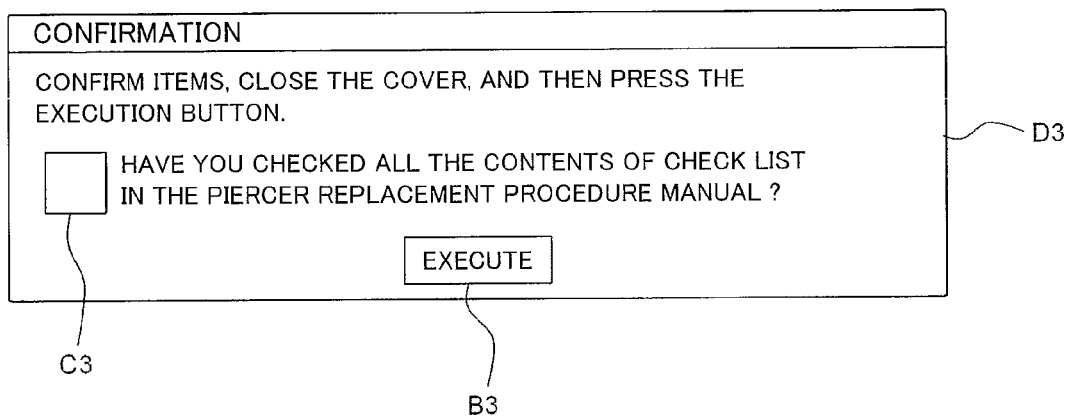
FIG. 11 shows an adjustment process confirmation dialogue.

Upon completion of mounting of a new piercer 5b, the user turns on the power of the sample analyzer 1. Upon activation of the sample analyzer 1, the post-piercer-replacement adjustment process is automatically executed. FIG. 10 is a flow chart showing the procedure of the post-piercer-replacement adjustment process. First, the CPU of the controller 3a causes the display unit 3b to display an adjustment process confirmation dialogue (S201). FIG. 11 shows the adjustment process confirmation dialogue. An adjustment process confirmation dialogue D3 includes a message that instructs the user to check all the contents in a check list in a piercer replacement procedure manual distributed to the user in advance, to confirm the check list, and then, to close the cover of the measurement mechanism unit 2 not shown and press the execution button. Further, to a side of the message "Have you checked the contents of the check list in the piercer replacement procedure manual?", a check box C3 selectable through operation of the input unit 3c is provided. Further, the adjustment process confirmation dialogue D3 is provided with an execution button B3 selectable through operation of the input unit 3c. The execution button B3 is configured such that the execution button B3 is not operable while no check mark is displayed in the check box C3, and is operable while the check box C3 is selected and a check mark is displayed.

After confirming the piercer replacement procedure manual, the user operates the input unit 3c and checks the check box C3 to select the execution button B3. The CPU of the controller 3a waits until receiving an execution instruction from the user (NO in S202). Upon receiving an execution instruction from the user as described above (YES in S202), the CPU of the controller 3a closes the adjustment process confirmation dialogue D3 (S203) and causes the display unit 3b to display an execution dialogue (S204).

Figure 12:
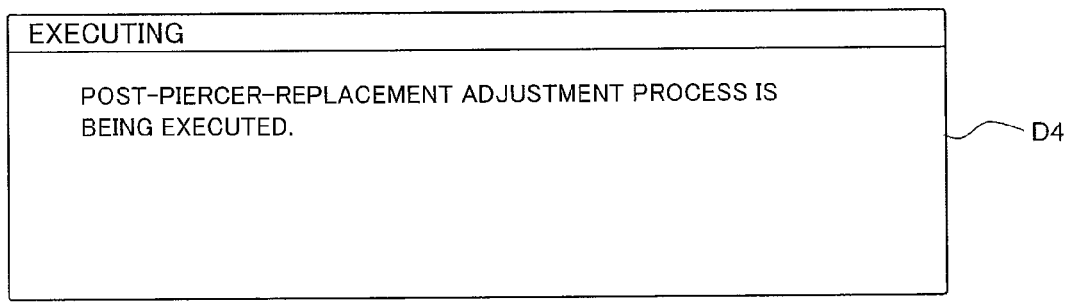
FIG. 12 shows an execution dialogue.

FIG. 12 shows the execution dialogue. An execution dialogue D4 includes a message "Post-piercer-replacement adjustment process is being executed." The CPU of the controller 3a causes the display unit 3b to display the execution dialogue D4, and instructs the controller 20 to execute a position information adjustment process such as a θ direction adjustment process and a Z direction adjustment process regarding the piercer 5b. In present embodiment, an execution instruction of the position information adjustment process is given by the user pressing the execution button in the adjustment process confirmation dialogue shown in FIG. 11. However, input of adjustment execution in the position information adjustment process is not limited thereto. For example, after a new piercer 5b has been mounted, an execution instruction may be automatically issued when the user turns on the power, or alternatively, a sensor may detect that the piercer 5b has been replaced with a new piercer 5b and an execution instruction may be automatically issued upon reception of the detection result.

Upon receiving the above-described instruction data from the controller 3a, first, the CPU 21 of the controller 20 determines whether the piercer 5b is present within an adjustment region (S205). In this process, the CPU 21 obtains information of the state of the origin sensor 57 from the θ motor control circuit 84, and determines, based on this information, whether light in the origin sensor 57 is blocked. When light in the origin sensor 57 is blocked, the CPU 21 determines that the piercer 5b is within the adjustment region including the sample aspiration position 300 being the replacement position, and when light in the origin sensor 57 is not blocked, the CPU 21 determines that the piercer 5b is at a position greatly distanced from the sample aspiration position 300, that is, the piercer 5b is not in the adjustment region. When having determined that the piercer 5b is not in the adjustment region (NO in S205), the CPU 21 executes a piercer replacement position search process (S206).

Figure 13:
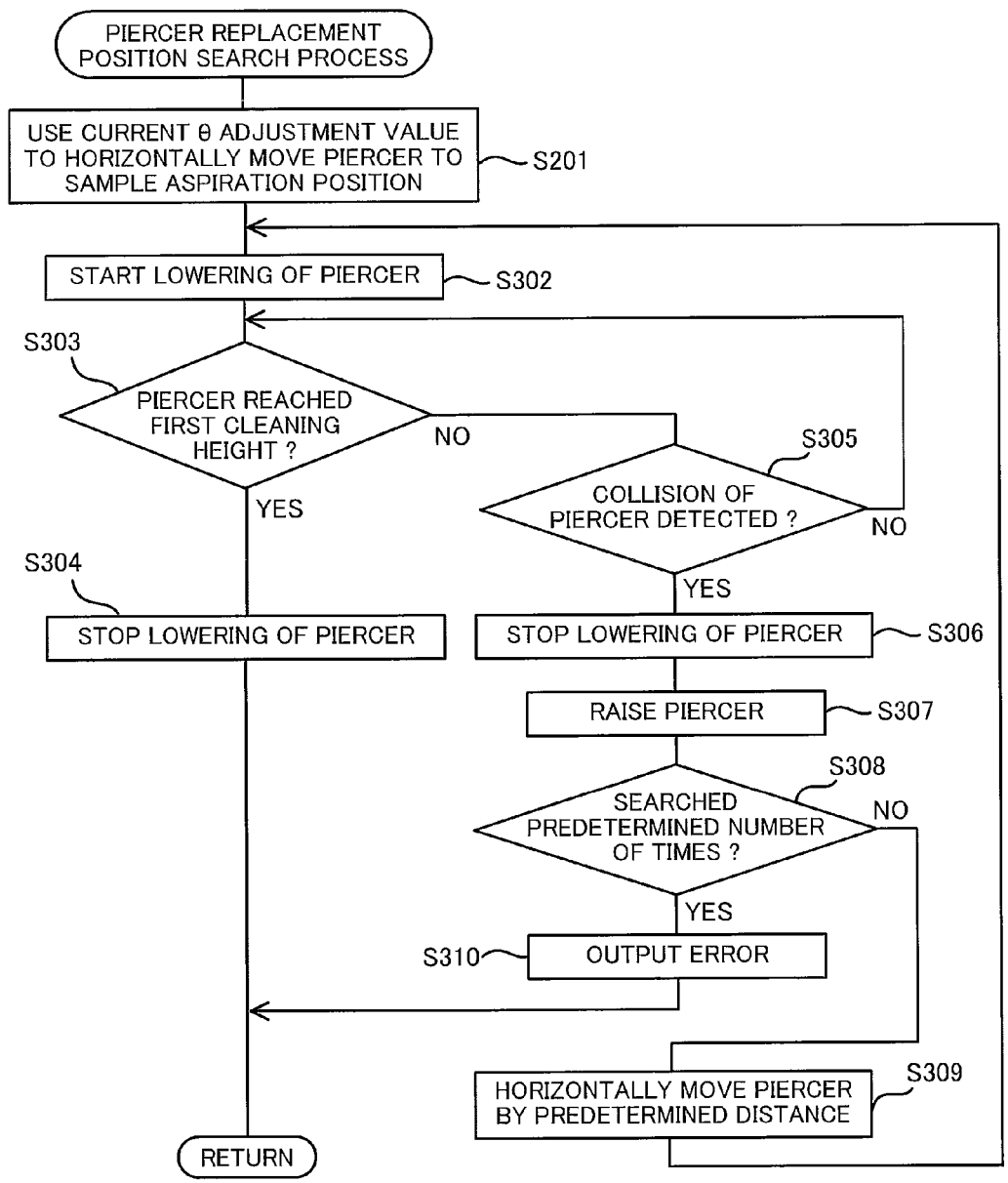
FIG. 13 is a flow chart showing a procedure of a piercer replacement position search process.

FIG. 13 is a flow chart showing the procedure of the piercer replacement position search process. As described above, in order to accurately move the piercer 5b to the sample aspiration position 300 or the like, a sample dispensing position being a predetermined position on the cuvette setting part 7, the cleaning position of the piercer cleaning part 49 or the like, the number of pulses of the θ drive motor 72a from the origin position to each position is needed. The memory 22 of the primary controller 20 has stored therein θ adjustment values indicating the number of pulses for these. In the piercer replacement position search process, first, the CPU 21 uses the corresponding current θ adjustment value to move the piercer 5b to above the sample aspiration position 300 (S301). That is, by driving the θ drive motor 72a by the current θ adjustment value from the origin position, the arm part 5a is pivoted until the piercer 5b is arranged above the sample aspiration position 300.

However, the θ adjustment value used in step S301 is data for the piercer 5b before the replacement. Thus, it may not necessarily the case that the piercer 5b can be accurately moved to above the sample aspiration position 300 by using this θ adjustment value, even after the replacement of the piercer 5b. Therefore, in the piercer replacement position search process, the CPU 21 determines, in the following manner, whether the piercer 5b is positioned above the sample aspiration position 300. When the piercer 5b is not positioned above the sample aspiration position 300, the CPU 21 corrects the position, so as to position the piercer 5b above the sample aspiration position 300.

First, the CPU 21 starts lowering of the piercer 5b by driving the Z drive motor 73a (S302). At this time, in order to allow the tip of the piercer 5b to enter the aspiration tube path 48a of the piercer cleaning part 48, the CPU 21 outputs a drive order such that the tip of the piercer 5b is lowered from the upper limit position by a predetermined distance.

At this time, if the piercer 5b is not accurately positioned relative to the sample aspiration position 300, the piercer 5b collides with a periphery of the path, not being able to enter the aspiration tube path 48a of the cleaning part 48, and thus, lowering of the piercer 5b stops.

The Z motor control circuit 82 determines whether the piercer 5b has been lowered to a first cleaning height that is below the upper limit position by the predetermined distance (S303). When the piercer 5b has been lowered to the first cleaning height (YES in S303), the Z motor control circuit 82 stops lowering of the arm part 5a (S304), and the secondary controller 80 transmits a drive stop report to the primary controller 20. Then, the CPU 21 returns the processing.

FIG. 14 is an enlarged side cross-sectional view of the piercer cleaning part 48 for describing the first cleaning height. As shown in FIG. 14, a height in the middle of the aspiration tube path 48a is the first cleaning height. When the piercer 5b is lowered by a predetermined distance in accordance with the drive order, the lower end of the piercer 5b reaches the first cleaning height.

When the tip of the piercer 5b has come into contact with an object before reaching the first cleaning height, a limit signal is outputted from the collision sensor 55 to the Z motor control circuit 82. When the piercer 5b has not reached the first cleaning height (NO in S303), the Z motor control circuit 82 determines whether collision of the piercer 5b has been detected based on the limit signal from the collision sensor 55 (S305). When having received a limit signal from the collision sensor 55, the Z motor control circuit 82 determines that collision of the piercer 5b has been detected (YES in S305), and stops the Z drive motor 73a (S306). At this time, an error report is outputted from the secondary controller 80 to the primary controller 20. On the other hand, when collision of the piercer 5b has not been detected in step S305, the Z motor control circuit 82 returns the processing to step S303, and continues lowering of the piercer 5b.

When collision of the piercer 5b has been detected and lowering of the piercer 5b has been stopped, the CPU 21 outputs a drive order to the secondary controller 80, whereby the Z drive motor 73a is driven, and the piercer 5b is raised to a predetermined position (S307). Next, the CPU 21 determines whether piercer replacement position search has been performed a predetermined number of times, that is, whether lowering of the piercer 5b has been performed the predetermined number of times (S308). When the number of times of search is less than the predetermined number of times (NO in S308), the CPU 21 outputs a drive order to drive the θ drive motor 72a in a predetermined direction by a predetermined pulses, thereby causing the arm part 5a to pivot in the predetermined direction by a predetermined distance (S309). As a result, the piercer 5b is horizontally moved by a predetermined distance.

After step S309, the CPU 21 returns the processing to step S302. Accordingly, the piercer 5b is lowered from the position obtained as a result of the horizontal movement. In this manner, piercer replacement position search is performed. When the piercer 5b has collided with a peripheral portion of the aspiration tube path 48a of the piercer cleaning part 48, the piercer 5b is raised again, horizontally moved by a predetermined distance, and then, lowered. When the number of times of such search has reached the predetermined number of times (YES in S308), the CPU 21 outputs error information (S310), this error information is provided to the controller 3a, and then the CPU of the controller 3a causes the display unit 3b to display error information indicating that setting of a θ adjustment value or a Z adjustment value after the replacement of the piercer has failed. After outputting the error information, the CPU 21 returns the processing.

When the piercer replacement position search process as described above has ended, the CPU 21 determines whether an error that the number of times of search has reached the predetermined number of times has occurred in the piercer replacement position search process (S207). When the error has occurred (YES in S207), the CPU 21 ends the processing.

When the error has not occurred in the piercer replacement position search process (NO in S207), or when the piercer 5b is within the adjustment region in step S205 (YES in S205), the CPU 21 executes the θ direction adjustment process (S208).

Figure 15:
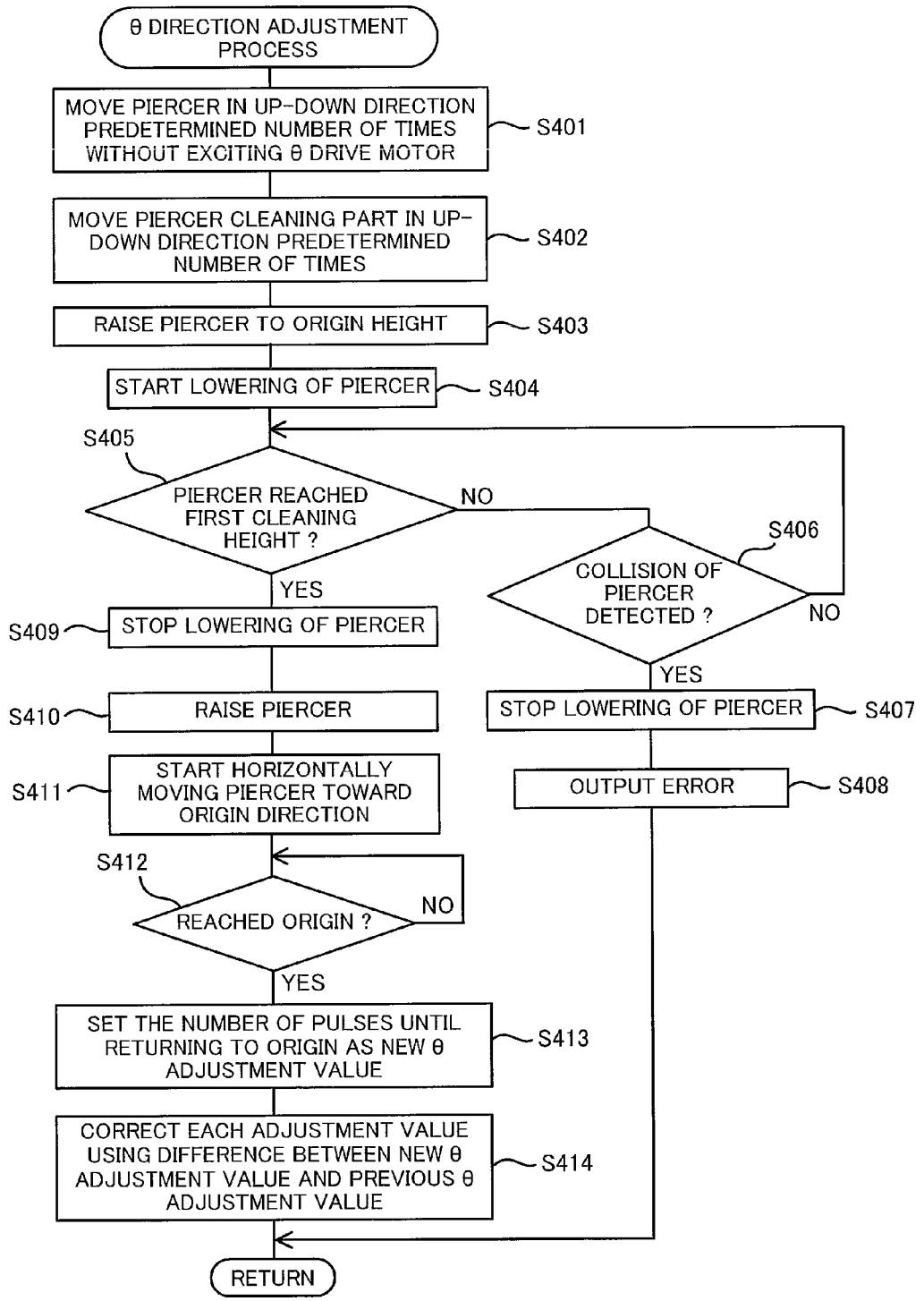
FIG. 15 is a flow chart showing a procedure of a θ direction adjustment process.

FIG. 15 is a flow chart showing the procedure of the θ direction adjustment process. First, the CPU 21 outputs a drive order to drive the Z drive motor without exciting the θ drive motor 72a, to reciprocate the arm part 5a in the up-down direction a plurality of times (S401). Further, the CPU 21 outputs a drive order to drive a motor not shown without exciting the θ drive motor 72a, to move the piercer cleaning part 48 in the up-down direction by a predetermined distance (S402). The processes of steps S401 and S402 are processes for accurately positioning the piercer 5b at the sample aspiration position 300 being a position at which the piercer 5b can be inserted into the aspiration tube path 48a of the piercer cleaning part 48. FIG. 16 is an enlarged side cross-sectional view of the piercer cleaning part 48 for describing positioning of the piercer 5b at the sample aspiration position 300. As shown in the upper view in FIG. 16, for example, a case is assumed that the piercer 5b is positioned closer to one side of the aspiration tube path 48a. Since the θ drive motor 72a is not excited, if a force in the horizontal direction is applied to the arm part 5a, the arm part 5a easily pivots. In this state, if the piercer 5b and the piercer cleaning part 48 reciprocate in the up-down direction relative to each other, a side face of the piercer 5b comes into contact with a side wall of the aspiration tube path 48a due to a tilt, bend, or the like of the piercer 5b, and the piercer 5b moves in the horizontal direction so as to be away from the side wall of the aspiration tube path 48a, toward the center of the aspiration tube path 48a, as shown in the lower view in FIG. 16. In this manner, the piercer 5b is accurately positioned at the sample aspiration position 300.

Next, the CPU 21 outputs a drive order to drive the Z drive motor 73a, to raise the piercer 5b to an origin height being an upper limit position (S403). Further, the CPU 21 outputs a drive order so as to lower the piercer 5b from the upper limit position to the first cleaning height, and starts lowering of the piercer 5b (S404). At this time, the Z drive motor 73a has been excited. Accordingly, it is confirmed whether the piercer 5b can be accurately inserted into the aspiration tube path 48a. At this time, if the piercer 5b is not accurately positioned relative to the sample aspiration position 300, the piercer 5b cannot enter the aspiration tube path 48a of the cleaning part 48 and collides with the periphery of the path.

The Z motor control circuit 82 determines whether the piercer 5b has been lowered to the first cleaning height (S405). When the tip of the piercer 5b has come into contact with an object before reaching the first cleaning height, a limit signal is outputted from the collision sensor 55 to the Z motor control circuit 82. When the piercer 5b has not reached the first cleaning height (NO in S405), the Z motor control circuit 82 determines whether collision of the piercer 5b has been detected based on the limit signal from the collision sensor 55 (S406). When having received the limit signal from the collision sensor 55, the Z motor control circuit 82 determines that collision of the piercer 5b has been detected (YES in S406), and stops the Z drive motor 73a (S407). At this time, an error report is outputted from the secondary controller 80 to the primary controller 20, and upon receiving this error report, the CPU 21 outputs error information (S408). This error information is provided to the controller 3a, and the CPU of the controller 3a causes the display unit 3b to display error information indicating that setting of a θ adjustment value or a Z adjustment value after the replacement of the piercer has failed. After outputting the error information, the CPU 21 returns the processing.

On the other hand, when collision of the piercer 5b has not been detected in step S406, the Z motor control circuit 82 returns the processing to step S405, and continues lowering of the piercer 5b.

In step S405, when the piercer 5b has been lowered to the first cleaning height (YES in S405), the Z motor control circuit 82 stops lowering of the arm part 5a (S409), and the secondary controller 80 transmits a drive stop report to the primary controller 20. In this case, the piercer 5b has been accurately positioned at the sample aspiration position 300. Upon receiving the drive stop report, the CPU 21 outputs drive orders to drive the Z drive motor 73a to raise the piercer 5b to the origin height being the upper limit position (S410), and further to drive the θ drive motor 72a to start pivoting of the arm part 5a (S411), thereby horizontally moving the piercer 5b toward the origin position 500. When light in the origin sensor 57 is blocked, a limit signal is outputted to the θ motor control circuit 84. By the θ motor control circuit 84 receiving this limit signal, pivot of the arm part 5a is stopped, and a drive stop report is outputted from the secondary controller 80 to the primary controller 20. The CPU 21 waits until receiving the drive stop signal (NO in S412), and determines, upon receiving the drive stop signal, that the piercer 5b has reached the origin position 500 (YES in S412).

Next, the CPU 21 obtains, from the secondary controller 80, the number of output pulses of the θ encoder 72b until the arm part 5a had reached the origin position 500, and sets this number of pulses as a new θ adjustment value for the sample aspiration position 300 (S413). Further, the CPU 21 calculates the difference between the new θ adjustment value and the preceding θ adjustment value, and corrects, by adding this difference, each of the θ adjustment value from the origin position 500 to the sample dispensing position, the θ adjustment value from the origin position 500 to the cleaning position of the piercer cleaning part 49, and the θ adjustment value from the origin position 500 to a reagent aspiration position (S414). Then, the CPU 21 returns the processing.

When the θ direction adjustment process as described above has ended, the CPU 21 determines whether an error of detecting collision of the piercer 5b has occurred in the θ direction adjustment process (S209). When the error has occurred (YES in S209), the CPU 21 ends the processing. When the error has not occurred in the θ direction adjustment process (NO in S209), the CPU 21 executes the Z direction adjustment process (S210).

Figure 17:
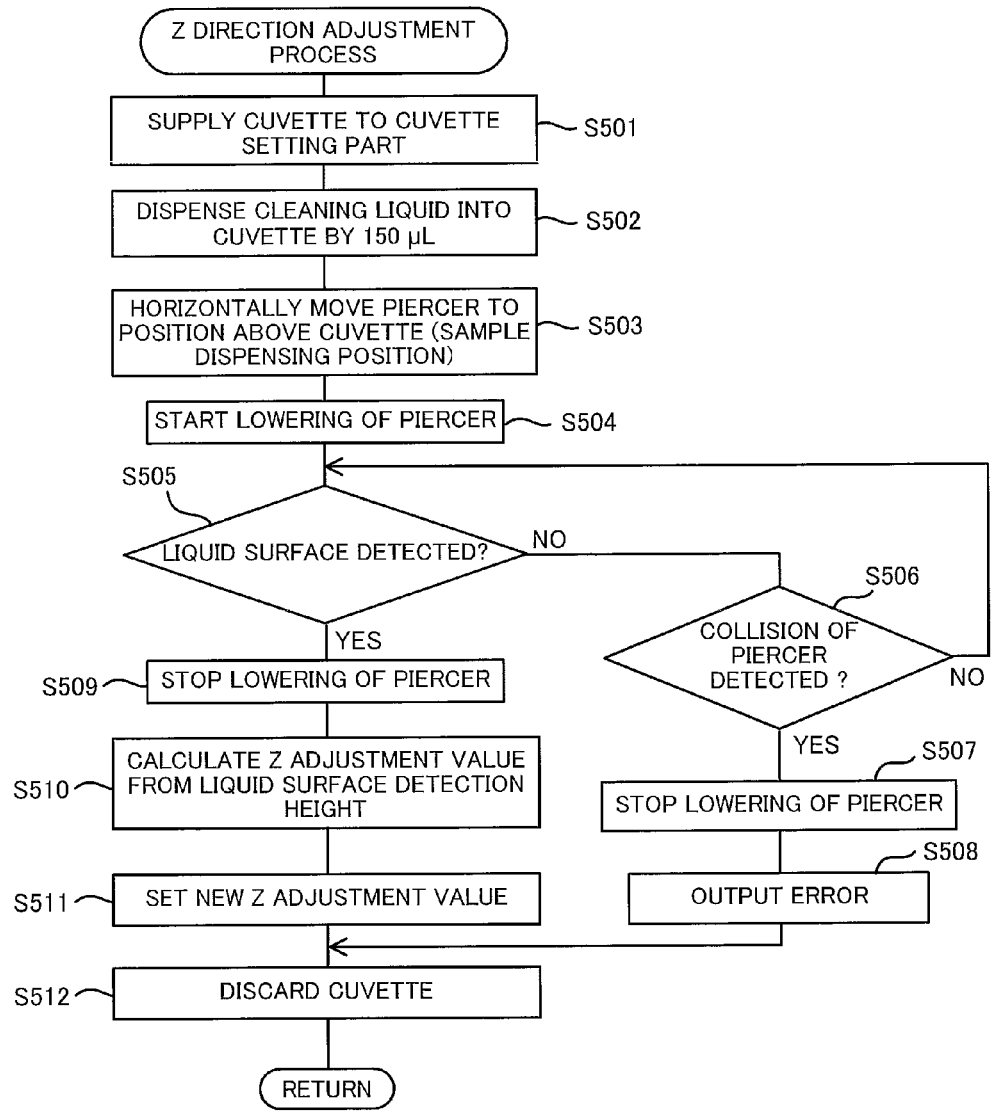
FIG. 17 is a flow chart showing a procedure of a Z direction adjustment process.

FIG. 17 is a flow chart showing the procedure of the Z direction adjustment process. First, the CPU 21 outputs drive orders to drive the cuvette setting part 7, the cuvette supplying part 15, and the catcher unit 17, to supply one cuvette 150 (see FIG. 2) at a predetermined position in the cuvette setting part 7 (S501). Subsequently, the cuvette setting part 7 to which the cuvette 150 has been supplied is rotated and the second sample dispensing arm 6 is driven, whereby a cleaning liquid (RO water) is dispensed into the cuvette by 150 μL (S502).

Next, the CPU 21 outputs a drive order to drive the θ drive motor 72a, to pivot the arm part 5a, such that the piercer 5b is horizontally moved to the sample dispensing position being a position above the cuvette 150 (S503). The CPU 21 outputs a drive order to drive the Z drive motor 73a, to start lowering of the piercer 5b (S504). When the tip of the piercer 5b has come into contact with the liquid surface of the cleaning liquid in the cuvette 150, the liquid surface sensor 56 detects this and outputs a limit signal. When the tip of the piercer 5b has come into contact with an object such as an upper end edge of the cuvette 150, the collision sensor 55 outputs a limit signal.

The Z motor control circuit 82 determines whether the liquid surface has been detected by the liquid surface sensor 56 (S505). When the liquid surface has not been detected (NO in S505), the Z motor control circuit 82 determines whether collision of the piercer 5b has been detected by the collision sensor 55 (S506). When having received a limit signal from the collision sensor 55, the Z motor control circuit 82 determines that collision of the piercer 5b has been detected (YES in S506) and stops the Z drive motor 73a (S507). At this time, an error report is outputted from the secondary controller 80 to the primary controller 20, and upon receiving this error report, the CPU 21 outputs error information (S508). This error information is provided to the controller 3a, and the CPU of the controller 3a causes the display unit 3b to display error information indicating that setting of a θ adjustment value or a Z adjustment value after the replacement of the piercer has failed. After outputting the error information, the CPU 21 returns the processing.

On the other hand, when collision of the piercer 5b has not been detected in step S506, the Z motor control circuit 82 returns the processing to step S505, and continues lowering of the piercer 5b.

Figure 18:
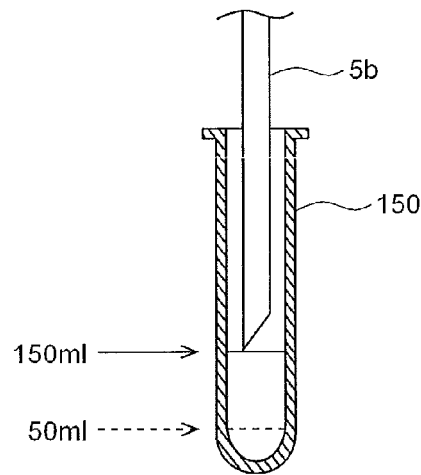
FIG. 18 is a side cross-sectional view of a cuvette for describing calculation of a Z adjustment value.

In step S505, when the liquid surface has been detected (YES in S505), the Z motor control circuit 82 stops lowering of the arm part 5a (S509), and the secondary controller 80 transmits a drive stop report to the primary controller 20. Upon receiving the drive stop report, the CPU 21 obtains, from the secondary controller 80, the number of output pulses of the Z encoder 73b until the piercer 5b had come into contact with the liquid surface, and calculates, based on this number of pulses, a Z adjustment value indicating the height of the liquid surface at a time when the liquid is held in the cuvette 150 by 50 μL (S510). FIG. 18 is a side cross-sectional view of a cuvette 150 for describing the calculation of the Z adjustment value. In the cuvette 150, 50 μL is a dead volume. When only an amount of 50 μL or less of the liquid is contained in the cuvette 150, aspiration of the liquid by a predetermined amount is not ensured by the piercer 5b or the pipette 6b. That is, when aspiration operation or dispensing operation is performed, the piercer 5b or the pipette 6b is not lowered to a position lower than or equal to the 50 μL liquid surface height in the cuvette 150, and the 50 μL liquid surface height is the lower limit height for lowering. The primary controller 20 sets this lower limit height as the Z adjustment value. Since the shape of the cuvette 150 is known, based on the liquid surface height at a time when 150 μL of the liquid is contained in the cuvette 150, the liquid surface height at a time when 50 μL of the liquid is contained in the cuvette 150 can be calculated. By using the number of output pulses of the Z encoder 73b obtained as described above, the CPU 21 calculates, as the Z adjustment value, the number of pulses from when the piercer 5b begins to be lowered from the origin height and until it comes into contact with the liquid surface of the liquid contained in the cuvette 150 by 50 μL.

It should be noted that a look-up table showing the relationship between the liquid surface height at a time when 150 μL of the liquid is contained in the cuvette 150 and the liquid surface height at a time when 50 μL of the liquid is contained in the cuvette 150 is stored in the memory 22 or the like in advance, and with reference to this look-up table, the liquid surface height at a time when 50 μL of the liquid is contained in the cuvette 150 may be derived based on the liquid surface height at a time when 150 μL of the liquid is contained in the cuvette 150.

The CPU 21 sets a new Z adjustment value calculated as described above (S511). Further, the CPU 21 outputs drive orders to drive the cuvette setting part 7 and the catcher unit 17, to transfer the cuvette 150 set in the cuvette setting part 7 to the discarding hole 19a (S512), thereby discarding the cuvette 150, and then returns the processing.

When the Z direction adjustment process as described above has ended, the CPU 21 determines whether an error of detecting collision of the piercer 5b has occurred in the Z direction adjustment process (S211). When the error has occurred (YES in S211), the CPU 21 ends the processing. When the error has not occurred in the Z direction adjustment process (NO in S211), the CPU 21 executes a cleaning position lowering confirmation process (S212).

Figure 19:
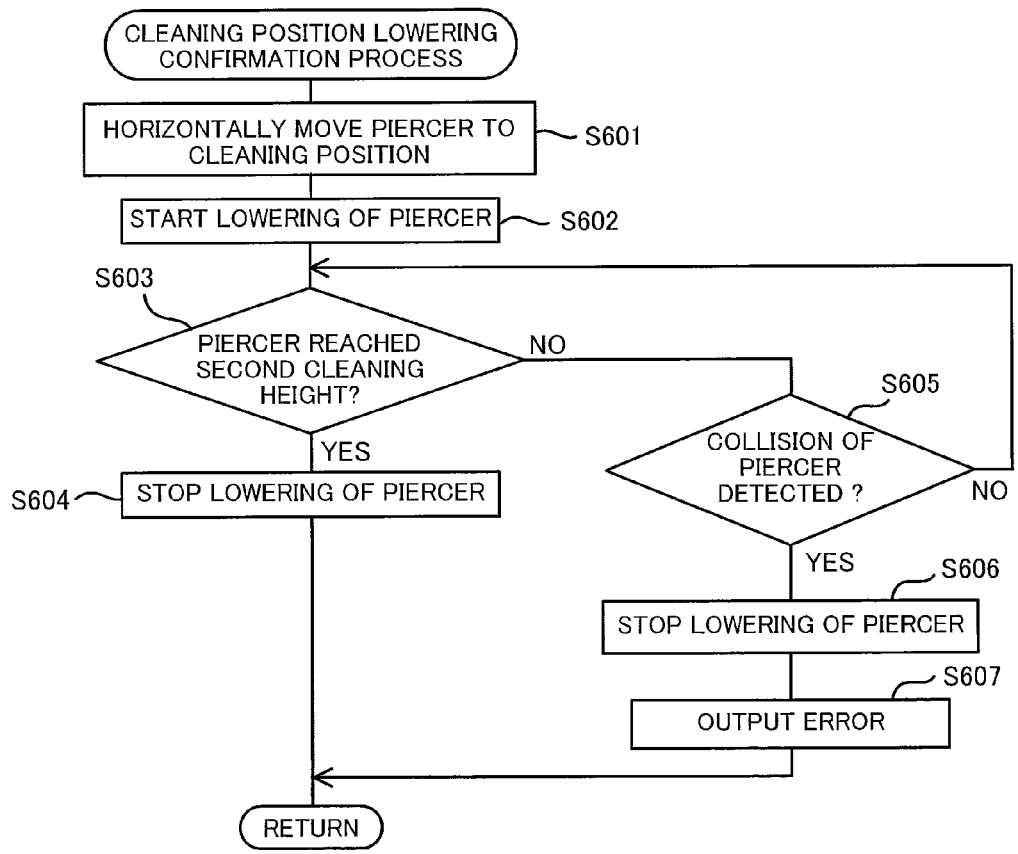
FIG. 19 is a flow chart showing a procedure of a cleaning position lowering confirmation process.

FIG. 19 is a flow chart showing the procedure of the cleaning position lowering confirmation process. First, the CPU 21 outputs a drive order to drive the θ drive motor 72a, to pivot the arm part 5a such that the piercer 5b is horizontally moved to the cleaning position above the piercer cleaning part 49 (S601). The CPU 21 outputs a drive order to drive the Z drive motor 73a, to start lowering of the piercer 5b (S602), thereby lowering the piercer 5b to a second cleaning height being a height at which the tip of the piercer 5b is inserted into the aspiration tube path 49a of the piercer cleaning part 49. Accordingly, it is confirmed whether the piercer 5b can be accurately inserted into the aspiration tube path 49a. At this time, if the piercer 5b is not accurately positioned relative to the cleaning position, the piercer 5b cannot enter the aspiration tube path 49a of the cleaning part 49 and collides with the periphery of the path.

The Z motor control circuit 82 determines whether the piercer 5b has been lowered to the second cleaning height (S603). When the piercer 5b has been lowered to the second cleaning height (YES in S603), the Z motor control circuit 82 stops lowering of the arm part 5a (S604), and the secondary controller 80 transmits a drive stop report to the primary controller 20. Then, the CPU 21 returns the processing.

When the tip of the piercer 5b has come into contact with an object before reaching the second cleaning height, a limit signal is outputted from the collision sensor 55 to the Z motor control circuit 82. When the piercer 5b has not reached the second cleaning height (NO in S603), the Z motor control circuit 82 determines whether collision of the piercer 5b has been detected based on the limit signal from the collision sensor 55 (S605). When collision of the piercer 5b has not been detected (NO in S605), the Z motor control circuit 82 returns the processing to step S603 and continues lowering of the piercer 5b. On the other hand, when collision of the piercer 5b has been detected in step S605 (YES in S605), the Z motor control circuit 82 stops the Z drive motor 73a (S606). At this time, an error report is outputted from the secondary controller 80 to the primary controller 20. Upon receiving the error report, the CPU 21 outputs error information (S607), this error information is provided to the controller 3a, and the CPU of the controller 3a causes the display unit 3b to display error information indicating that setting of a θ adjustment value or a Z adjustment value after the replacement of the piercer has failed. After outputting the error information, the CPU 21 returns the processing.

When the cleaning position lowering confirmation process as described above has ended, the CPU 21 outputs a drive order to drive the Z drive motor 73a, to raise the piercer 5b to the origin height (upper limit position), further outputs a drive order to drive the θ drive motor 72a, to horizontally move the piercer 5b to the origin position 500 (S213), and then ends the processing.

Figure 20:
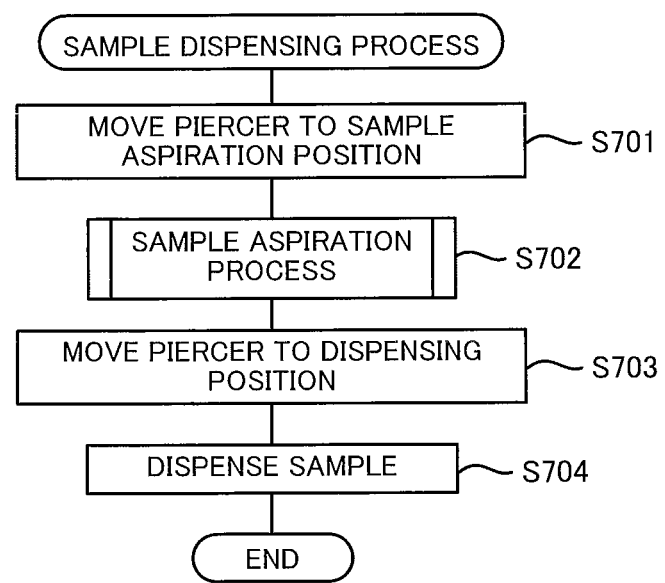
FIG. 20 is a flow chart showing a procedure of a sample dispensing process.

The θ adjustment value and the Z adjustment value set in the post-piercer-replacement adjustment process as described above are used in a sample dispensing process. FIG. 20 is a flow chart showing the procedure of the sample dispensing process. First, the CPU 21 outputs a drive order that designates the θ adjustment value for the sample aspiration position 300 to drive the θ drive motor 72a, to pivot the arm part 5a such that the piercer 5b is horizontally moved to the sample aspiration position 300 (S701). Next, the CPU 21 executes a sample aspiration process (S702).

Figure 21:
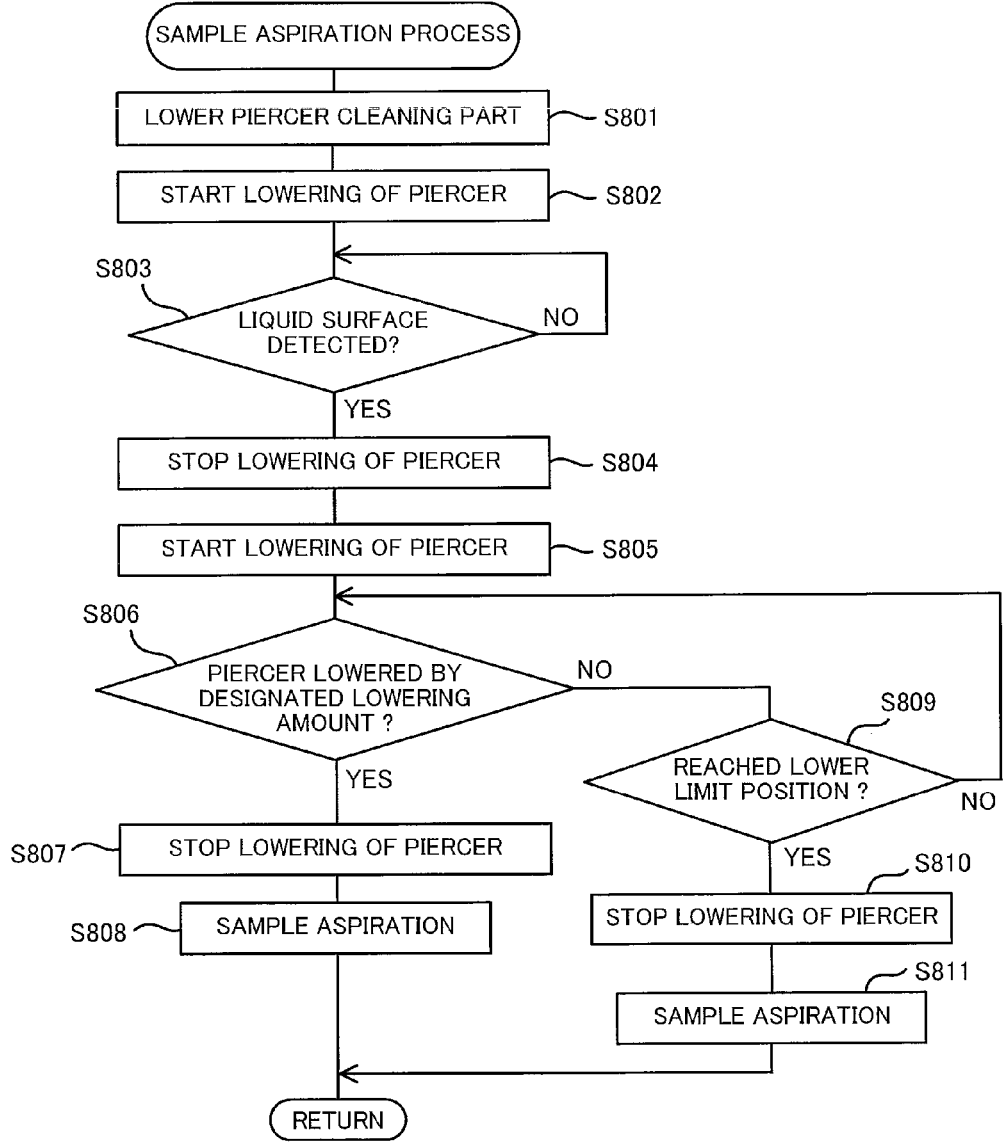
FIG. 21 is a flow chart showing a procedure of a sample aspiration process.

FIG. 21 is a flow chart showing the procedure of the sample aspiration process. First, the CPU 21 outputs a drive order to drive a motor not shown, to lower the piercer cleaning part 48 by a predetermined amount (S801). As a result, the cap 101 of the sample container 100 is pressed downwardly.

Next, the CPU 21 outputs a drive order to drive the Z drive motor 73a, to start lowering of the piercer 5b (S802). The piercer 5b passes through the aspiration tube path 48a of the piercer cleaning part 48, and is further lowered to pass through the cap 101 of the sample container 100. When the tip of the piercer 5b has come into contact with the liquid surface of the sample in the sample container 100, the liquid surface sensor 56 detects this and outputs a limit signal. The Z motor control circuit 82 determines whether the liquid surface has been detected by the liquid surface sensor 56 (S803). When the liquid surface has not been detected (NO in S803), the Z motor control circuit 82 returns the processing to step S803 again, and continues lowering of the piercer 5b until the liquid surface is detected. When the liquid surface has been detected (YES in S803), the Z motor control circuit 82 stops lowering of the arm part 5a (S804).

After the liquid surface has been detected and lowering of the piercer 5b has been stopped as described above, the CPU 21 outputs a drive order instructing that the piercer 5b is to be lowered by a lowering amount specified in accordance with an aspiration amount of the sample, within the range not exceeding the lower limit position specified by the Z adjustment value, so as to start lowering of the piercer 5b (S805). The above aspiration amount of the sample is specified in accordance with each measurement item designated in a measurement order of the sample.

The Z motor control circuit 82 determines whether the piercer 5b has been lowered by the number of pulses designated by the drive order, that is, by the designated lowering amount (S806). When the piercer 5b has been lowered by the designated lowering amount (YES in S806), the Z motor control circuit 82 stops lowering of the arm part 5a (S807), and the secondary controller 80 transmits a drive stop report to the primary controller 20. Upon receiving the drive stop report, the CPU 21 outputs a drive order to drive the syringe motor 74c, to cause the piercer 5b to aspirate the sample by the above aspiration amount from the sample container 100 (S808). After the aspiration of the sample has been completed, the CPU 21 returns the processing. In a case where the Z motor control circuit 82 has failed in driving the Z drive motor 73a by the designated number of pulses because the designated number of pulses exceeds the Z adjustment value, that is, in a case where the piercer 5b has not been lowered by the designated lowering amount, when the number of drive pulses of the Z drive motor 73a has become equal to the Z adjustment value, the Z motor control circuit 82 stops drive of the Z drive motor 73a and outputs an error report.

On the other hand, when the lowering amount of the piercer 5b is less than the designated lowering amount in step S806 (NO in S806), the Z motor control circuit 82 determines whether the piercer 5b has reached the lower limit position (S809). That is, the Z motor control circuit 82 compares the number of drive pulses of the Z drive motor 73a at that time point with the Z adjustment value. When the number of drive pulses is greater than or equal to the Z adjustment value, the Z motor control circuit 82 determines that the piercer 5b has reached the lower limit position. When the piercer 5b has not reached the lower limit position (NO in S809), the Z motor control circuit 82 returns the processing to step S806 and continues lowering of the piercer 5b. On the other hand, when it is determined that the piercer 5b has reached the lower limit position in step S809 (YES in S809), the Z motor control circuit 82 stops the Z drive motor 73a (S810). At this time, an error report is outputted from the secondary controller 80 to the primary controller 20. Upon receiving the error report, the CPU 21 outputs error information (S811), this error information is provided to the controller 3a, and the CPU of the controller 3a causes the display unit 3b to display error information indicating that sample aspiration has failed. After outputting the error information, the CPU 21 returns the processing.

When the sample aspiration process as described above has ended, the CPU 21 determines whether an error (failure of sample aspiration) has occurred in the sample aspiration process. When the error has occurred, the CPU 21 ends the processing. When the error has not occurred in the sample aspiration process, the CPU 21 outputs a drive order that designates the θ adjustment value for the sample dispensing position to drive the θ drive motor 72a, to pivot the arm part 5a such that the piercer 5b is horizontally moved to the sample aspiration position 300. Then, the CPU 21 outputs a drive order to drive the Z drive motor 73a, to lower the arm part 5a, thereby lowering the piercer 5b until the piercer 5b enters the inside of the cuvette 150 set in the cuvette setting part 7 (S703). Thereafter, the CPU 21 outputs a drive order to drive the syringe motor 74c, to cause the piercer 5b to dispense the sample into the cuvette 150 (S704). After dispensing of the sample has been completed, the CPU 21 ends the processing.

The sample analyzer 1 is configured to be used by each operator having different operation authorization logging in, in accordance with his or her authorization. Such authorization includes various types of authorization such as: service person authorization which is used by a dedicated service person sent from the manufacturer/seller of the sample analyzer when the service person performs repair or maintenance of the analyzer, and user authorization which is used by a general user such as a clinical laboratory technician or the like who actually uses the analyzer in an medical institution where the sample analyzer is installed when the general user uses the analyzer. The piercer replacement preparation process and the post-piercer-replacement adjustment process described above are configured to be able to be executed while the operator has logged in using his or her user authorization. Accordingly, when a general user of the analyzer such as a clinical laboratory technician performs unfamiliar piercer replacing operation which is not often performed, the user can perform piercer position adjustment operation simply and assuredly. It is understood that the piercer replacement preparation process and the post-piercer-replacement adjustment process may be configured to be able to be executed when a user has logged in using his or her service person authorization.

Through the configuration as described above, by the post-piercer-replacement adjustment process being executed, a θ adjustment value and a Z adjustment value for the replaced piercer 5b are automatically set. Thus, operational burden on the user in piercer replacing operation is reduced. Further, by the liquid surface sensor 56 detecting contact of the piercer 5b with the liquid surface, the Z adjustment value is set. Thus, damage of the replaced piercer 5b is avoided. Further, since the pipette 6b provided separately from the piercer 5b supplies the cleaning liquid to the cuvette 150, it is not necessary to supply the cleaning liquid to the cuvette 150 by using the piercer 5b for which the Z adjustment value has not been set yet. Thus, the cleaning liquid can be assuredly supplied and there is no risk of damaging the piercer 5b due to collision or the like of the piercer 5b to the cuvette 150.

Further, since the θ direction adjustment process is executed before the Z direction adjustment process, when the piercer 5b is to be positioned at the sample dispensing position in the Z direction adjustment process, the θ adjustment value set in the θ direction adjustment process can be used. Thus, the piercer 5b can be accurately positioned at the sample dispensing position.

Other Embodiments

The embodiment described above has described a case where the piercer is to be replaced. However, the present invention is not limited thereto. A pipette whose lower end is formed flat can be replaced. Further, although the configuration of the sample analyzer 1 being a blood coagulation analyzer has been described, the present invention is not limited thereto. Analyzers for laboratory tests such as biochemical analyzer, immunoanalyzer, blood cell counter, and urine analyzer may have similar configuration regarding replacement of the pipette or piercer.

In the embodiment described above, 150 μL of the cleaning liquid is supplied to a cuvette 150 and based on the liquid surface height thereof, the liquid surface height at a time when 50 μL of cleaning liquid is contained in the cuvette 150 is determined to be used as the Z adjustment value. However, the present invention is not limited thereto. For example, 50 μL of the cleaning liquid is supplied to the cuvette 150, and the liquid surface height thereof is directly set to be the Z adjustment value. Further, the liquid such as the cleaning liquid is supplied not to the cuvette but to a liquid containing part provided to the measurement mechanism unit 2, and based on the liquid surface height thereof, the Z adjustment value may be determined.

In the embodiment described above, the liquid surface height detected by the liquid surface sensor 56 is set as the Z adjustment value, and in the sample dispensing process performed thereafter, lowering operation of the piercer 5b by the Z motor control circuit 82 is changed. However, the present invention is not limited thereto. For example, the mounting height of the piercer 5b can be automatically adjusted by the analyzer based on the liquid surface height detected by the liquid surface sensor 56. Further, based on the liquid surface height detected by the liquid surface sensor 56, the position itself which serves as a start point for operation of the first sample dispensing arm 5 provided with the piercer 5b may be changed.

What is claimed is:

1. A sample detector comprising:
   a piercer which is a metal tube member and is used to aspirate a sample, wherein a lower end of the piercer is formed sharp so as to be able to pass through a cap of a sample container;
   a dispensing arm comprising a tube for supplying liquid to a liquid container and is configured to move the tube;
   a motorized movement mechanism for moving the piercer;
   a liquid surface sensor for detecting contact of the piercer with a liquid surface;
   a detector for measuring a measurement specimen including the sample; and
   a controller configured to execute operations, comprising:
      receiving an instruction to replace the piercer; and
      moving the piercer to a piercer replacement position to replace the piercer with a replacement piercer, wherein
   the sample detector which receives the instruction to replace the piercer also receives an instruction to turn off power of the sample detector,
   the sample detector which receives the instruction to turn off power of the sample detector also receives an instruction to turn on power of the sample detector, and the controller is configured to, upon receiving the instruction to replace the piercer, execute a replacement preparation process in which the piercer is moved by the movement mechanism to the piercer replacement position prior to power being turned off, and the replacement of the piercer takes place with power being turned off; and
   the controller of the sample detector which receives the instruction to turn on power of the sample detector, is configured to execute operations, comprising:
      moving the tube to be supplied with the liquid;
      supplying the liquid to the liquid container using the tube;
      lowering the replacement piercer toward the liquid container containing the liquid supplied by the tube; and
      obtain information of a vertical height position of the replacement piercer based on a detection by the liquid surface sensor through contacting between the replacement piercer and the liquid surface in the liquid container which the liquid is supplied by the tube.

2. The sample detector of claim 1, wherein the controller is configured to, when sample analysis is performed, move the replacement piercer by the motorized movement mechanism, based on the obtained information of the vertical height position of the replacement piercer.

3. The sample detector of claim 1, wherein the detector is further configured to measure a measurement specimen including the sample and a reagent.

4. The sample detector of claim 1, wherein the liquid container is a cuvette and the liquid container is supplied by the tube with the sample or a reagent for sample analysis, wherein the tube supplies the sample or a reagent to the liquid container which is a cuvette for sample analysis.

5. The sample detector of claim 1, wherein the controller is configured to execute a piercer adjustment operation upon receiving an input for executing adjustment of the replacement piercer.

6. The sample detector of claim 5, wherein the controller is configured to, when executing the piercer adjustment operation, execute a piercer setting process for setting a set value regarding the vertical height position of the replacement piercer, based on the obtained information of the vertical height position of the replacement piercer, and configured to, when sample analysis is performed, move the replacement piercer by the motorized movement mechanism, based on the set value set in the piercer setting process.

7. The sample detector of claim 1, further comprising:
a cuvette supplying part comprising a cuvette stocker which stores a plurality of the liquid containers, the cuvette supplying part includes a transporting catcher arm to transport the stored liquid containers in the cuvette supplying part to a cuvette setting part by, wherein
the controller is configured to, in a piercer adjustment operation, supply the liquid container to the cuvette setting part by the cuvette supplying part.

8. The sample detector of claim 7, wherein the controller is configured to, in a piercer adjustment operation, supply the liquid container to the cuvette setting part by the cuvette supplying part, before supplying the liquid by the tube to the liquid container set on the cuvette setting part.

9. The sample detector of claim 1, wherein the motorized movement mechanism is configured to move the replacement piercer in a horizontal direction, and
the controller is configured to, in a piercer adjustment operation, execute a horizontal direction set value setting process for setting a set value regarding a position in the horizontal direction of the replacement piercer before lowering the replacement piercer toward the liquid container by the motorized movement mechanism.

10. The sample detector of claim 9, further comprising:
an aspiration tube path being a hole formed in a cap portion of the liquid container, which the aspiration tube path allows the replacement piercer to be inserted thereinto, wherein
the controller is configured to, in the horizontal direction set value setting process, position the replacement piercer in the horizontal direction, by the replacement piercer being moved in a vertical direction by the motorized movement mechanism while the replacement piercer is inserted in the hole of the aspiration tube path.

11. The sample detector of claim 10, wherein the controller is configured to, in the horizontal direction set value setting process, determine whether the replacement piercer is inserted in the hole of the aspiration tube path before the replacement piercer is moved in the vertical direction by the motorized movement mechanism while the replacement piercer is inserted in the hole of the aspiration tube path.

12. The sample detector of claim 1, further comprising:
a transporting catcher arm which transports the liquid container; and
a discarding opening for receiving a discarded liquid container, wherein the controller is configured to, in a piercer adjustment operation, transport the liquid container from a cuvette setting part to the discarding opening by the transporting catcher arm, after obtaining the information regarding the position in the height direction of the replacement piercer.

13. The sample detector of claim 12, wherein the transporting catcher arm transports the liquid container which contains the sample or reagent supplied by the tube for sample analysis.

* * * * *